United States Patent
Orme et al.

(10) Patent No.: US 7,288,261 B2
(45) Date of Patent: Oct. 30, 2007

(54) MID-LIFE VACCINE AND METHODS FOR BOOSTING ANTI-MYCOBACTERIAL IMMUNITY

(75) Inventors: Ian M. Orme, Fort Collins, CO (US); John T. Belisle, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 340 days.

(21) Appl. No.: 10/332,512

(22) PCT Filed: Jul. 10, 2001

(86) PCT No.: PCT/US01/21717

§ 371 (c)(1),
(2), (4) Date: Nov. 24, 2003

(87) PCT Pub. No.: WO02/04018

PCT Pub. Date: Jan. 17, 2002

(65) Prior Publication Data

US 2004/0180056 A1    Sep. 16, 2004

Related U.S. Application Data

(60) Provisional application No. 60/217,646, filed on Jul. 10, 2000.

(51) Int. Cl.
*A61K 39/04* (2006.01)
*A61K 49/00* (2006.01)
*A61K 39/00* (2006.01)

(52) U.S. Cl. .............. 424/248.1; 424/9.1; 424/9.2; 424/184.1; 424/185.1; 424/190.1; 424/234.1; 424/278.1; 435/243; 435/253.1; 530/300; 530/350

(58) Field of Classification Search ............ 424/9.1, 424/9.2, 184.1, 185.1, 190.1, 234.1, 248.1, 424/278.1; 435/243, 253.1; 530/300, 350
See application file for complete search history.

(56) References Cited

U.S. PATENT DOCUMENTS

| | | | | |
|---|---|---|---|---|
| 5,714,593 A | * | 2/1998 | Laqueyrerie et al. | 536/23.1 |
| 5,916,558 A | * | 6/1999 | Content et al. | 424/130.1 |
| 5,955,356 A | * | 9/1999 | Content et al. | 435/325 |
| 6,495,347 B1 | * | 12/2002 | Siegel et al. | 435/69.7 |
| 6,734,173 B1 | * | 5/2004 | Wu et al. | 514/44 |

FOREIGN PATENT DOCUMENTS

| | | | |
|---|---|---|---|
| WO | WO95/01441 | * | 1/1995 |
| WO | WO96/19578 | * | 6/1996 |
| WO | WO96/37219 | * | 11/1996 |
| WO | WO98/16645 | * | 4/1998 |
| WO | WO88/06591 | * | 9/1998 |
| WO | WO98/44119 | * | 10/1998 |
| WO | WO99/02670 | * | 1/1999 |

* cited by examiner

*Primary Examiner*—Rodney P Swartz
(74) *Attorney, Agent, or Firm*—Browdy and Neimark, PLLC

(57) ABSTRACT

Vaccine compositions for boosting immunity to mycobacteria when administered in mid-life in a subject who has been vaccinated neonatally or in early childhood with BCG and in whom protective immunity has waned comprise one or more purified immunogenic proteins from *Mycobacterium tuberculosis* from a group of 30 proteins that stimulate T cell immunity and interferon-γ secretion. A preferred protein is Ag85A, the secreted product (SEQ ID NO:31) of the Rv3084c gene. Also disclosed are methods for boosting immunity in such BCG-vaccinated subjects comprising administering an effective amount of the above vaccine composition.

39 Claims, 8 Drawing Sheets

SEQUENCE LISTING

<160> NUMBER OF SEQ ID NOS: 31

<210> SEQ ID NO 1
<211> LENGTH: 338
<212> TYPE: PRT
<213> ORGANISM: Mycobacterium tuberculosis

<400> SEQUENCE: 1

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

```
Gly Ala Val Gly Gly Thr Ala Thr Ala Gly Ala Phe Ser Arg Pro Gly
             35                  40                  45

Leu Pro Val Glu Tyr Leu Gln Val Pro Ser Pro Ser Met Gly Arg Asp
 50                  55                  60

Ile Lys Val Gln Phe Gln Ser Gly Ala Asn Ser Pro Ala Leu Tyr
 65                  70                  75                  80

Leu Leu Asp Gly Leu Arg Ala Gln Asp Phe Ser Gly Trp Asp Ile
                 85                  90                  95

Asn Thr Pro Ala Phe Glu Trp Tyr Asp Gln Ser Gly Leu Ser Val Val
                100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
            130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
                180                 185                 190

Ser Gly Leu Leu Asp Pro Ser Gln Ala Met Gly Pro Thr Leu Ile Gly
            195                 200                 205

Leu Ala Met Gly Asp Ala Gly Gly Tyr Lys Ala Ser Asp Met Trp Gly
210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
            275                 280                 285

Ala Gly Gly Gly His Asn Gly Val Phe Asp Phe Pro Asp Ser Gly Thr
            290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala

<210> SEQ ID NO 2
<211> LENGTH: 325
<212> TYPE: PRT
<213> ORGANISM: Mycobacterium tuberculosis

<400> SEQUENCE: 2

Met Thr Asp Val Ser Arg Lys Ile Arg Ala Trp Gly Arg Arg Leu Met
 1               5                  10                  15

Ile Gly Thr Ala Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
 50                  55                  60
```

-continued

```
Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 3
<211> LENGTH: 340
<212> TYPE: PRT
<213> ORGANISM: Mycobacterium tuberculosis

<400> SEQUENCE: 3

Met Thr Phe Phe Glu Gln Val Arg Arg Leu Arg Ser Ala Ala Thr Thr
1               5                   10                  15

Leu Pro Arg Arg Leu Ala Ile Ala Ala Met Gly Ala Val Leu Val Tyr
            20                  25                  30

Gly Leu Val Gly Thr Phe Gly Gly Pro Ala Thr Ala Gly Ala Phe Ser
        35                  40                  45

Arg Pro Gly Leu Pro Val Glu Tyr Leu Gln Val Pro Ser Ala Ser Met
    50                  55                  60

Gly Arg Asp Ile Lys Val Gln Phe Gln Gly Gly Gly Pro His Ala Val
65                  70                  75                  80

Tyr Leu Leu Asp Gly Leu Arg Ala Gln Asp Asp Tyr Asn Gly Trp Asp
                85                  90                  95

Ile Asn Thr Pro Ala Phe Glu Glu Tyr Tyr Gln Ser Gly Leu Ser Val
```

-continued

```
                100                 105                 110
Ile Met Pro Val Gly Gly Gln Ser Ser Phe Tyr Thr Asp Trp Tyr Gln
            115                 120                 125

Pro Ser Gln Ser Asn Gly Gln Asn Tyr Thr Tyr Lys Trp Glu Thr Phe
        130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
    210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
            260                 265                 270

Leu Glu Gly Leu Thr Leu Arg Thr Asn Gln Thr Phe Arg Asp Thr Tyr
        275                 280                 285

Ala Ala Asp Gly Gly Arg Asn Gly Val Phe Asn Phe Pro Pro Asn Gly
    290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Ala Ala Pro Ala
                325                 330                 335

Ala Pro Ala Ala
            340

<210> SEQ ID NO 4
<211> LENGTH: 325
<212> TYPE: PRT
<213> ORGANISM: Mycobacterium tuberculosis

<400> SEQUENCE: 4

Met His Gln Val Asp Pro Asn Leu Thr Arg Arg Lys Gly Arg Leu Ala
1               5                   10                  15

Ala Leu Ala Ile Ala Ala Met Ala Ser Ala Ser Leu Val Thr Val Ala
            20                  25                  30

Val Pro Ala Thr Ala Asn Ala Asp Pro Glu Pro Ala Pro Pro Val Pro
        35                  40                  45

Thr Thr Ala Ala Ser Pro Ser Thr Ala Ala Pro Pro Ala Pro
    50                  55                  60

Ala Thr Pro Val Ala Pro Pro Pro Ala Ala Ala Asn Thr Pro Asn
65                  70                  75                  80

Ala Gln Pro Gly Asp Pro Asn Ala Ala Pro Pro Ala Asp Pro Asn
                85                  90                  95

Ala Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125
```

```
Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Arg Leu Gly Ser Asp
            180                 185                 190

Met Gly Glu Phe Tyr Met Pro Tyr Pro Gly Thr Arg Ile Asn Gln Glu
            195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
                260                 265                 270

Lys Gly Ala Ala Lys Ala Leu Ala Glu Ser Ile Arg Pro Leu Val Ala
                275                 280                 285

Pro Pro Pro Ala Pro Ala Pro Ala Pro Ala Glu Pro Ala Pro Ala Pro
    290                 295                 300

Ala Pro Ala Gly Glu Val Ala Pro Thr Pro Thr Thr Pro Thr Pro Gln
305                 310                 315                 320

Arg Thr Leu Pro Ala
                325

<210> SEQ ID NO 5
<211> LENGTH: 374
<212> TYPE: PRT
<213> ORGANISM: Mycobacterium tuberculosis

<400> SEQUENCE: 5

Val Lys Ile Arg Leu His Thr Leu Leu Ala Val Leu Thr Ala Ala Pro
1               5                   10                  15

Leu Leu Leu Ala Ala Ala Gly Cys Gly Ser Lys Pro Pro Ser Gly Ser
                20                  25                  30

Pro Glu Thr Gly Ala Gly Ala Gly Thr Val Ala Thr Thr Pro Ala Ser
            35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
                100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175
```

-continued

```
Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Ala Gly Phe
        275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
        355                 360                 365

Ile Ala Thr Ile Ser Ser
    370

<210> SEQ ID NO 6
<211> LENGTH: 261
<212> TYPE: PRT
<213> ORGANISM: Mycobacterium tuberculosis

<400> SEQUENCE: 6

Met Pro Lys Arg Ser Glu Tyr Arg Gln Gly Thr Pro Asn Trp Val Asp
1               5                   10                  15

Leu Gln Thr Thr Asp Gln Ser Ala Ala Lys Lys Phe Tyr Thr Ser Leu
            20                  25                  30

Phe Gly Trp Gly Tyr Asp Asp Asn Pro Val Pro Gly Gly Gly Gly Val
        35                  40                  45

Tyr Ser Met Ala Thr Leu Asn Gly Glu Ala Val Ala Ala Ile Ala Pro
    50                  55                  60

Met Pro Pro Gly Ala Pro Glu Gly Met Pro Pro Ile Trp Asn Thr Tyr
65                  70                  75                  80

Ile Ala Val Asp Asp Val Asp Ala Val Val Asp Lys Val Val Pro Gly
                85                  90                  95

Gly Gly Gln Val Met Met Pro Ala Phe Asp Ile Gly Asp Ala Gly Arg
            100                 105                 110

Met Ser Phe Ile Thr Asp Pro Thr Gly Ala Ala Val Gly Leu Trp Gln
        115                 120                 125

Ala Asn Arg His Ile Gly Ala Thr Leu Val Asn Glu Thr Gly Thr Leu
    130                 135                 140

Ile Trp Asn Glu Leu Leu Thr Asp Lys Pro Asp Leu Ala Leu Ala Phe
145                 150                 155                 160

Tyr Glu Ala Val Val Gly Leu Thr His Ser Ser Met Glu Ile Ala Ala
```

```
                    165                 170                 175
Gly Gln Asn Tyr Arg Val Leu Lys Ala Gly Asp Ala Glu Val Gly Gly
            180                 185                 190

Cys Met Glu Pro Pro Met Pro Gly Val Pro Asn His Trp His Val Tyr
        195                 200                 205

Phe Ala Val Asp Asp Ala Asp Ala Thr Ala Ala Lys Ala Ala Ala Ala
        210                 215                 220

Gly Gly Gln Val Ile Ala Glu Pro Ala Asp Ile Pro Ser Val Gly Arg
225                 230                 235                 240

Phe Ala Val Leu Ser Asp Pro Gln Gly Ala Ile Phe Ser Val Leu Lys
                245                 250                 255

Pro Ala Pro Gln Gln
            260

<210> SEQ ID NO 7
<211> LENGTH: 162
<212> TYPE: PRT
<213> ORGANISM: Mycobacterium tuberculosis

<400> SEQUENCE: 7

Val Thr Asp Met Asn Pro Asp Ile Glu Lys Asp Gln Thr Ser Asp Glu
1               5                   10                  15

Val Thr Val Glu Thr Thr Ser Val Phe Arg Ala Asp Phe Leu Ser Glu
            20                  25                  30

Leu Asp Ala Pro Ala Gln Ala Gly Thr Glu Ser Ala Val Ser Gly Val
        35                  40                  45

Glu Gly Leu Pro Pro Gly Ser Ala Leu Leu Val Val Lys Arg Gly Pro
    50                  55                  60

Asn Ala Gly Ser Arg Phe Leu Leu Asp Gln Ala Ile Thr Ser Ala Gly
65                  70                  75                  80

Arg His Pro Asp Ser Asp Ile Phe Leu Asp Asp Val Thr Val Ser Arg
                85                  90                  95

Arg His Ala Glu Phe Arg Leu Glu Asn Asn Glu Phe Asn Val Val Asp
            100                 105                 110

Val Gly Ser Leu Asn Gly Thr Tyr Val Asn Arg Glu Pro Val Asp Ser
        115                 120                 125

Ala Val Leu Ala Asn Gly Asp Glu Val Gln Ile Gly Lys Phe Arg Leu
    130                 135                 140

Val Phe Leu Thr Gly Pro Lys Gln Gly Glu Asp Asp Gly Ser Thr Gly
145                 150                 155                 160

Gly Pro

<210> SEQ ID NO 8
<211> LENGTH: 181
<212> TYPE: PRT
<213> ORGANISM: Mycobacterium tuberculosis

<400> SEQUENCE: 8

Met Thr Glu Tyr Glu Gly Pro Lys Thr Lys Phe His Ala Leu Met Gln
1               5                   10                  15

Glu Gln Ile His Asn Glu Phe Thr Ala Ala Gln Tyr Val Ala Ile
            20                  25                  30

Ala Val Tyr Phe Asp Ser Glu Asp Leu Pro Gln Leu Ala Lys His Phe
        35                  40                  45

Tyr Ser Gln Ala Val Glu Glu Arg Asn His Ala Met Met Leu Val Gln
    50                  55                  60
```

-continued

```
His Leu Leu Asp Arg Asp Leu Arg Val Glu Ile Pro Gly Val Asp Thr
 65                  70                  75                  80

Val Arg Asn Gln Phe Asp Arg Pro Arg Glu Ala Leu Ala Leu Ala Leu
                 85                  90                  95

Asp Gln Glu Arg Thr Val Thr Asp Gln Val Gly Arg Leu Thr Ala Val
            100                 105                 110

Ala Arg Asp Glu Gly Asp Phe Leu Gly Glu Gln Phe Met Gln Trp Phe
        115                 120                 125

Leu Gln Glu Gln Ile Glu Val Ala Leu Met Ala Thr Leu Val Arg
    130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ser Gly Ala Pro His Ala
                165                 170                 175

Ala Gly Gly Arg Leu
            180
```

<210> SEQ ID NO 9
<211> LENGTH: 165
<212> TYPE: PRT
<213> ORGANISM: Mycobacterium tuberculosis

<400> SEQUENCE: 9

```
Met Ala Gln Ile Thr Leu Arg Gly Asn Ala Ile Asn Thr Val Gly Glu
 1               5                  10                  15

Leu Pro Ala Val Gly Ser Pro Ala Pro Ala Phe Thr Leu Thr Gly Gly
                 20                  25                  30

Asp Leu Gly Val Ile Ser Ser Asp Gln Phe Arg Gly Lys Ser Val Leu
            35                  40                  45

Leu Asn Ile Phe Pro Ser Val Asp Thr Pro Val Cys Ala Thr Ser Val
        50                  55                  60

Arg Thr Phe Asp Glu Arg Ala Ala Ala Ser Gly Ala Thr Val Leu Cys
 65                  70                  75                  80

Val Ser Lys Asp Leu Pro Phe Ala Gln Lys Arg Phe Cys Gly Ala Glu
                 85                  90                  95

Gly Thr Glu Asn Val Met Pro Ala Ser Ala Phe Arg Asp Ser Phe Gly
            100                 105                 110

Glu Asp Tyr Gly Val Thr Ile Ala Asp Gly Pro Met Ala Gly Leu Leu
        115                 120                 125

Ala Arg Ala Ile Val Val Ile Gly Ala Asp Gly Asn Val Ala Tyr Thr
    130                 135                 140

Glu Leu Val Pro Glu Ile Ala Gln Glu Pro Asn Tyr Glu Ala Ala Leu
145                 150                 155                 160

Ala Ala Leu Gly Ala
                165
```

<210> SEQ ID NO 10
<211> LENGTH: 123
<212> TYPE: PRT
<213> ORGANISM: Mycobacterium tuberculosis

<400> SEQUENCE: 10

```
Met Ala Arg Thr Leu Ala Leu Arg Ala Ser Ala Gly Leu Val Ala Gly
 1               5                  10                  15

Met Ala Met Ala Ala Ile Thr Leu Ala Pro Gly Ala Arg Ala Glu Thr
                 20                  25                  30
```

-continued

```
Gly Glu Gln Phe Pro Gly Asp Gly Val Phe Leu Val Gly Thr Asp Ile
        35                  40                  45

Ala Pro Gly Thr Tyr Arg Thr Glu Gly Pro Ser Asn Pro Leu Ile Leu
    50                  55                  60

Val Phe Gly Arg Val Ser Glu Leu Ser Thr Cys Ser Trp Ser Thr His
65                  70                  75                  80

Ser Ala Pro Glu Val Ser Asn Glu Asn Ile Val Asp Thr Asn Thr Ser
                85                  90                  95

Met Gly Pro Met Ser Val Val Ile Pro Pro Thr Val Ala Ala Phe Gln
            100                 105                 110

Thr His Asn Cys Lys Leu Trp Met Arg Ile Ser
        115                 120
```

<210> SEQ ID NO 11
<211> LENGTH: 100
<212> TYPE: PRT
<213> ORGANISM: Mycobacterium tuberculosis

<400> SEQUENCE: 11

```
Val Ala Lys Val Asn Ile Lys Pro Leu Glu Asp Lys Ile Leu Val Gln
1               5                   10                  15

Ala Asn Glu Ala Glu Thr Thr Thr Ala Ser Gly Leu Val Ile Pro Asp
            20                  25                  30

Thr Ala Lys Glu Lys Pro Gln Glu Gly Thr Val Val Ala Val Gly Pro
        35                  40                  45

Gly Arg Trp Asp Glu Asp Gly Glu Lys Arg Ile Pro Leu Asp Val Ala
    50                  55                  60

Glu Gly Asp Thr Val Ile Tyr Ser Lys Tyr Gly Gly Thr Glu Ile Lys
65                  70                  75                  80

Tyr Asn Gly Glu Glu Tyr Leu Ile Leu Ser Ala Arg Asp Val Leu Ala
                85                  90                  95

Val Val Ser Lys
            100
```

<210> SEQ ID NO 12
<211> LENGTH: 95
<212> TYPE: PRT
<213> ORGANISM: Mycobacterium tuberculosis

<400> SEQUENCE: 12

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 13
<211> LENGTH: 118
<212> TYPE: PRT
<213> ORGANISM: Mycobacterium tuberculosis

```
<400> SEQUENCE: 13

Met Gln Leu Gln Arg Thr Met Gly Gln Cys Arg Pro Met Arg Met Leu
1               5                   10                  15

Val Ala Leu Leu Leu Ser Ala Ala Thr Met Ile Gly Leu Ala Ala Pro
                20                  25                  30

Gly Lys Ala Asp Pro Thr Gly Asp Asp Ala Ala Phe Leu Ala Ala Leu
            35                  40                  45

Asp Gln Ala Gly Ile Thr Tyr Ala Asp Pro Gly His Ala Ile Thr Ala
    50                  55                  60

Ala Lys Ala Met Cys Gly Leu Cys Ala Asn Gly Val Thr Gly Leu Gln
65                  70                  75                  80

Leu Val Ala Asp Leu Arg Asp Tyr Asn Pro Gly Leu Thr Met Asp Ser
                85                  90                  95

Ala Ala Lys Phe Ala Ala Ile Ala Ser Gly Ala Tyr Cys Pro Glu His
            100                 105                 110

Leu Glu His His Pro Ser
            115

<210> SEQ ID NO 14
<211> LENGTH: 228
<212> TYPE: PRT
<213> ORGANISM: Mycobacterium tuberculosis

<400> SEQUENCE: 14

Val Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
                20                  25                  30

Lys Gly Thr Asp Thr Gly Gln Ala Cys Gln Ile Gln Met Ser Asp Pro
            35                  40                  45

Ala Tyr Asn Ile Asn Ile Ser Leu Pro Ser Tyr Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
                85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
            115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
            180                 185                 190

Thr Asn Asp Gly Val Ile Phe Phe Asn Pro Gly Glu Leu Leu Pro
            195                 200                 205

Glu Ala Ala Gly Pro Thr Gln Val Leu Val Pro Arg Ser Ala Ile Asp
    210                 215                 220

Ser Met Leu Ala
225
```

<210> SEQ ID NO 15
<211> LENGTH: 625
<212> TYPE: PRT
<213> ORGANISM: Mycobacterium tuberculosis

<400> SEQUENCE: 15

```
Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg
```

-continued

```
            370                 375                 380
Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
                420                 425                 430

Leu Thr Gly Ile Pro Pro Ala Pro Arg Gly Ile Pro Gln Ile Glu Val
                435                 440                 445

Thr Phe Asp Ile Asp Ala Asn Gly Ile Val His Val Thr Ala Lys Asp
        450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Glu Glu Ala Asp Val Arg Asn Gln
                500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
                580                 585                 590

Gly Ala Ala His Pro Gly Gly Glu Pro Gly Gly Ala His Pro Gly Ser
                595                 600                 605

Ala Asp Asp Val Val Asp Ala Glu Val Val Asp Asp Gly Arg Glu Ala
        610                 615                 620

Lys
625

<210> SEQ ID NO 16
<211> LENGTH: 359
<212> TYPE: PRT
<213> ORGANISM: Mycobacterium tuberculosis

<400> SEQUENCE: 16

Met Arg Ser Thr Val Ala Val Ala Val Ala Ala Val Ile Ala Ala
1               5                   10                  15

Ser Ser Gly Cys Gly Ser Asp Gln Pro Ala His Lys Ala Ser Gln Ser
                20                  25                  30

Met Ile Thr Pro Thr Thr Gln Ile Ala Gly Ala Gly Val Leu Gly Asn
                35                  40                  45

Asp Arg Lys Pro Asp Glu Ser Cys Ala Arg Ala Ala Ala Ala Asp
    50                  55                  60

Pro Gly Pro Pro Thr Arg Pro Ala His Asn Ala Ala Gly Val Ser Pro
65                  70                  75                  80

Glu Met Val Gln Val Pro Ala Glu Ala Gln Arg Ile Val Val Leu Ser
                85                  90                  95

Gly Asp Gln Leu Asp Ala Leu Cys Ala Leu Gly Leu Gln Ser Arg Ile
                100                 105                 110
```

Val Ala Ala Ala Leu Pro Asn Ser Ser Ser Gln Pro Ser Tyr Leu
            115                 120                 125

Gly Thr Thr Val His Asp Leu Pro Gly Val Gly Thr Arg Ser Ala Pro
130                 135                 140

Asp Leu Arg Ala Ile Ala Ala His Pro Asp Leu Ile Leu Gly Ser
145                 150                 155                 160

Gln Gly Leu Thr Pro Gln Leu Tyr Pro Gln Leu Ala Ala Ile Ala Pro
                165                 170                 175

Thr Val Phe Thr Ala Ala Pro Gly Ala Asp Trp Glu Asn Asn Leu Arg
            180                 185                 190

Gly Val Gly Ala Ala Thr Ala Arg Ile Ala Ala Val Asp Ala Leu Ile
        195                 200                 205

Thr Gly Phe Ala Glu His Ala Thr Gln Val Gly Thr Lys His Asp Ala
    210                 215                 220

Thr His Phe Gln Ala Ser Ile Val Gln Leu Thr Ala Asn Thr Met Arg
225                 230                 235                 240

Val Tyr Gly Ala Asn Asn Phe Pro Ala Ser Val Leu Ser Ala Val Gly
                245                 250                 255

Val Asp Arg Pro Pro Ser Gln Arg Phe Thr Asp Lys Ala Tyr Ile Glu
            260                 265                 270

Ile Gly Thr Thr Ala Ala Asp Leu Ala Lys Ser Pro Asp Phe Ser Ala
        275                 280                 285

Ala Asp Ala Asp Ile Val Tyr Leu Ser Cys Ala Ser Glu Ala Ala Ala
    290                 295                 300

Glu Arg Ala Ala Val Ile Leu Asp Ser Asp Pro Trp Arg Lys Leu Ser
305                 310                 315                 320

Ala Asn Arg Asp Asn Arg Val Phe Val Val Asn Asp Gln Val Trp Gln
                325                 330                 335

Thr Gly Glu Gly Met Val Ala Ala Arg Gly Ile Val Asp Asp Leu Arg
            340                 345                 350

Trp Val Asp Ala Pro Ile Asn
            355

<210> SEQ ID NO 17
<211> LENGTH: 164
<212> TYPE: PRT
<213> ORGANISM: Mycobacterium tuberculosis

<400> SEQUENCE: 17

Val Ala Gly Asp Thr Thr Ile Thr Ile Val Gly Asn Leu Thr Ala Asp
1               5                   10                  15

Pro Glu Leu Arg Phe Thr Pro Ser Gly Ala Ala Val Ala Asn Phe Thr
            20                  25                  30

Val Ala Ser Thr Pro Arg Ile Tyr Asp Arg Gln Thr Gly Glu Trp Lys
        35                  40                  45

Asp Gly Glu Ala Leu Phe Leu Arg Cys Asn Ile Trp Arg Glu Ala Ala
    50                  55                  60

Glu Asn Val Ala Glu Ser Leu Thr Arg Gly Ala Arg Val Ile Val Ser
65                  70                  75                  80

Gly Arg Leu Lys Gln Arg Ser Phe Glu Thr Arg Glu Gly Glu Lys Arg
                85                  90                  95

Thr Val Ile Glu Val Glu Val Asp Glu Ile Gly Pro Ser Leu Arg Tyr
            100                 105                 110

Ala Thr Ala Lys Val Asn Lys Ala Ser Arg Ser Gly Gly Phe Gly Ser
        115                 120                 125

```
Gly Ser Arg Pro Ala Pro Ala Gln Thr Ser Ser Ala Ser Gly Asp Asp
    130                 135                 140

Pro Trp Gly Ser Ala Pro Ala Ser Gly Ser Phe Gly Gly Asp Asp
145                 150                 155                 160

Glu Pro Pro Phe

<210> SEQ ID NO 18
<211> LENGTH: 130
<212> TYPE: PRT
<213> ORGANISM: Mycobacterium tuberculosis

<400> SEQUENCE: 18

Met Ala Lys Leu Ser Thr Asp Glu Leu Leu Asp Ala Phe Lys Glu Met
1               5                   10                  15

Thr Leu Leu Glu Leu Ser Asp Phe Val Lys Lys Phe Glu Glu Thr Phe
            20                  25                  30

Glu Val Thr Ala Ala Ala Pro Val Ala Val Ala Ala Gly Ala Ala
                35                  40                  45

Pro Ala Gly Ala Ala Val Glu Ala Ala Glu Gln Ser Glu Phe Asp
 50                  55                  60

Val Ile Leu Glu Ala Ala Gly Asp Lys Lys Ile Gly Val Ile Lys Val
65                  70                  75                  80

Val Arg Glu Ile Val Ser Gly Leu Gly Leu Lys Glu Ala Lys Asp Leu
                85                  90                  95

Val Asp Gly Ala Pro Lys Pro Leu Leu Glu Lys Val Ala Lys Glu Ala
                100                 105                 110

Ala Asp Glu Ala Lys Ala Lys Leu Glu Ala Ala Gly Ala Thr Val Thr
            115                 120                 125

Val Lys
    130

<210> SEQ ID NO 19
<211> LENGTH: 266
<212> TYPE: PRT
<213> ORGANISM: Mycobacterium tuberculosis

<400> SEQUENCE: 19

Met Thr Asn Ile Val Val Leu Ile Lys Gln Val Pro Asp Thr Trp Ser
1               5                   10                  15

Glu Arg Lys Leu Thr Asp Gly Asp Phe Thr Leu Asp Arg Glu Ala Ala
            20                  25                  30

Asp Ala Val Leu Asp Glu Ile Asn Glu Arg Ala Val Glu Glu Ala Leu
            35                  40                  45

Gln Ile Arg Glu Lys Glu Ala Ala Asp Gly Ile Glu Gly Ser Val Thr
 50                  55                  60

Val Leu Thr Ala Gly Pro Glu Arg Ala Thr Glu Ala Ile Arg Lys Ala
65                  70                  75                  80

Leu Ser Met Gly Ala Asp Lys Ala Val His Leu Lys Asp Asp Gly Met
                85                  90                  95

His Gly Ser Asp Val Ile Gln Thr Gly Trp Ala Leu Ala Arg Ala Leu
                100                 105                 110

Gly Thr Ile Glu Gly Thr Glu Leu Val Ile Ala Gly Asn Glu Ser Thr
            115                 120                 125

Asp Gly Val Gly Gly Ala Val Pro Ala Ile Ile Ala Glu Tyr Leu Gly
            130                 135                 140
```

```
Leu Pro Gln Leu Thr His Leu Arg Lys Val Ser Ile Glu Gly Gly Lys
145                 150                 155                 160

Ile Thr Gly Glu Arg Glu Thr Asp Glu Gly Val Phe Thr Leu Glu Ala
                165                 170                 175

Thr Leu Pro Ala Val Ile Ser Val Asn Glu Lys Ile Asn Glu Pro Arg
            180                 185                 190

Phe Pro Ser Phe Lys Gly Ile Met Ala Ala Lys Lys Glu Val Thr
        195                 200                 205

Val Leu Thr Leu Ala Glu Ile Gly Val Glu Ser Asp Glu Val Gly Leu
    210                 215                 220

Ala Asn Ala Gly Ser Thr Val Leu Ala Ser Thr Pro Lys Pro Ala Lys
225                 230                 235                 240

Thr Ala Gly Glu Lys Val Thr Asp Glu Gly Glu Gly Gly Asn Gln Ile
                245                 250                 255

Val Gln Tyr Leu Val Ala Gln Lys Ile Ile
            260                 265

<210> SEQ ID NO 20
<211> LENGTH: 318
<212> TYPE: PRT
<213> ORGANISM: Mycobacterium tuberculosis

<400> SEQUENCE: 20

Met Ala Glu Val Leu Val Leu Val Glu His Ala Glu Gly Ala Leu Lys
1               5                   10                  15

Lys Val Ser Ala Glu Leu Ile Thr Ala Ala Arg Ala Leu Gly Glu Pro
            20                  25                  30

Ala Ala Val Val Gly Val Pro Gly Thr Ala Ala Pro Leu Val Asp
        35                  40                  45

Gly Leu Lys Ala Ala Gly Ala Ala Lys Ile Tyr Val Ala Glu Ser Asp
    50                  55                  60

Leu Val Asp Lys Tyr Leu Ile Thr Pro Ala Val Asp Val Leu Ala Gly
65                  70                  75                  80

Leu Ala Glu Ser Ser Ala Pro Ala Gly Val Leu Ile Ala Ala Thr Ala
                85                  90                  95

Asp Gly Lys Glu Ile Ala Gly Arg Leu Ala Ala Arg Ile Gly Ser Gly
            100                 105                 110

Leu Leu Val Asp Val Val Asp Val Arg Glu Gly Gly Val Gly Val His
        115                 120                 125

Ser Ile Phe Gly Gly Ala Phe Thr Val Glu Ala Gln Ala Asn Gly Asp
    130                 135                 140

Thr Pro Val Ile Thr Val Arg Ala Gly Ala Val Glu Ala Glu Pro Ala
145                 150                 155                 160

Ala Gly Ala Gly Glu Gln Val Ser Val Glu Val Pro Ala Ala Glu
                165                 170                 175

Asn Ala Ala Arg Ile Thr Ala Arg Glu Pro Ala Val Ala Gly Asp Arg
            180                 185                 190

Pro Glu Leu Thr Glu Ala Thr Ile Val Val Ala Gly Arg Gly Val
        195                 200                 205

Gly Ser Ala Glu Asn Phe Ser Val Val Glu Ala Leu Ala Asp Ser Leu
    210                 215                 220

Gly Ala Ala Val Gly Ala Ser Arg Ala Ala Val Asp Ser Gly Tyr Tyr
225                 230                 235                 240

Pro Gly Gln Phe Gln Val Gly Gln Thr Gly Lys Thr Val Ser Pro Gln
                245                 250                 255
```

```
Leu Tyr Ile Ala Leu Gly Ile Ser Gly Ala Ile Gln His Arg Ala Gly
            260                 265                 270

Met Gln Thr Ser Lys Thr Ile Val Ala Val Asn Lys Asp Glu Glu Ala
            275                 280                 285

Pro Ile Phe Glu Ile Ala Asp Tyr Gly Val Val Gly Asp Leu Phe Lys
            290                 295                 300

Val Ala Pro Gln Leu Thr Glu Ala Ile Lys Ala Arg Lys Gly
305                 310                 315

<210> SEQ ID NO 21
<211> LENGTH: 195
<212> TYPE: PRT
<213> ORGANISM: Mycobacterium tuberculosis

<400> SEQUENCE: 21

Met Pro Leu Leu Thr Ile Gly Asp Gln Phe Pro Ala Tyr Gln Leu Thr
1               5                   10                  15

Ala Leu Ile Gly Gly Asp Leu Ser Lys Val Asp Ala Lys Gln Pro Gly
            20                  25                  30

Asp Tyr Phe Thr Thr Ile Thr Ser Asp Glu His Pro Gly Lys Trp Arg
        35                  40                  45

Val Val Phe Phe Trp Pro Lys Asp Phe Thr Phe Val Cys Pro Thr Glu
    50                  55                  60

Ile Ala Ala Phe Ser Lys Leu Asn Asp Glu Phe Glu Asp Arg Asp Ala
65                  70                  75                  80

Gln Ile Leu Gly Val Ser Ile Asp Ser Glu Phe Ala His Phe Gln Trp
                85                  90                  95

Arg Ala Gln His Asn Asp Leu Lys Thr Leu Pro Phe Pro Met Leu Ser
            100                 105                 110

Asp Ile Lys Arg Glu Leu Ser Gln Ala Ala Gly Val Leu Asn Ala Asp
        115                 120                 125

Gly Val Ala Asp Arg Val Thr Phe Ile Val Asp Pro Asn Asn Glu Ile
    130                 135                 140

Gln Phe Val Ser Ala Thr Ala Gly Ser Val Gly Arg Asn Val Asp Glu
145                 150                 155                 160

Val Leu Arg Val Leu Asp Ala Leu Gln Ser Asp Glu Leu Cys Ala Cys
                165                 170                 175

Asn Trp Arg Lys Gly Asp Pro Thr Leu Asp Ala Gly Glu Leu Leu Lys
            180                 185                 190

Ala Ser Ala
        195

<210> SEQ ID NO 22
<211> LENGTH: 540
<212> TYPE: PRT
<213> ORGANISM: Mycobacterium tuberculosis

<400> SEQUENCE: 22

Met Ala Lys Thr Ile Ala Tyr Asp Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60
```

```
Tyr Glu Lys Ile Gly Ala Glu Leu Val Lys Glu Val Ala Lys Thr
 65                  70                  75                  80

Asp Asp Val Ala Gly Asp Gly Thr Thr Thr Ala Thr Val Leu Ala Gln
                 85                  90                  95

Ala Leu Val Arg Glu Gly Leu Arg Asn Val Ala Ala Gly Ala Asn Pro
                100                 105                 110

Leu Gly Leu Lys Arg Gly Ile Glu Lys Ala Val Glu Lys Val Thr Glu
                115                 120                 125

Thr Leu Leu Lys Gly Ala Lys Glu Val Glu Thr Lys Glu Gln Ile Ala
            130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
            195                 200                 205

Gln Glu Ala Val Leu Glu Asp Pro Tyr Ile Leu Leu Val Ser Ser Lys
        210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
        290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
        370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
        450                 455                 460

Lys Val Arg Asn Leu Pro Ala Gly His Gly Leu Asn Ala Gln Thr Gly
465                 470                 475                 480
```

-continued

```
Val Tyr Glu Asp Leu Leu Ala Ala Gly Val Ala Asp Pro Val Lys Val
            485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Lys Glu Lys Ala Ser
            515                 520                 525

Val Pro Gly Gly Gly Asp Met Gly Gly Met Asp Phe
    530                 535                 540

<210> SEQ ID NO 23
<211> LENGTH: 144
<212> TYPE: PRT
<213> ORGANISM: Mycobacterium tuberculosis

<400> SEQUENCE: 23

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
            35                  40                  45

Gly Arg Tyr Glu Val Arg Ala Glu Leu Pro Gly Val Asp Pro Asp Lys
        50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
            115                 120                 125

Ser Glu Gly Lys Pro Thr Glu Lys His Ile Gln Ile Arg Ser Thr Asn
            130                 135                 140

<210> SEQ ID NO 24
<211> LENGTH: 143
<212> TYPE: PRT
<213> ORGANISM: Mycobacterium tuberculosis

<400> SEQUENCE: 24

Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
            20                  25                  30

Ile Gly Ala Leu Pro Ile Cys Gly Asp Asp Asp Arg Leu His Gly Met
            35                  40                  45

Leu Thr Asp Arg Asp Ile Val Ile Lys Gly Leu Ala Ala Gly Leu Asp
        50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
            115                 120                 125
```

Val Gln Phe Val Lys Ala Ile Cys Ser Pro Met Ala Leu Ala Ser
    130                 135                 140

<210> SEQ ID NO 25
<211> LENGTH: 75
<212> TYPE: PRT
<213> ORGANISM: Mycobacterium tuberculosis

<400> SEQUENCE: 25

Met Leu Gly Ala Asp Gln Ala Arg Ala Gly Pro Ala Arg Ile Trp
1               5                   10                  15

Arg Glu His Ser Met Ala Met Lys Pro Arg Thr Gly Asp Gly Pro
                20                  25                  30

Leu Glu Ala Thr Lys Glu Gly Arg Gly Ile Val Met Arg Val Pro Leu
            35                  40                  45

Glu Gly Gly Gly Arg Leu Val Val Glu Leu Thr Pro Asp Glu Ala Ala
    50                  55                  60

Ala Leu Gly Asp Glu Leu Lys Gly Val Thr Ser
65                  70                  75

<210> SEQ ID NO 26
<211> LENGTH: 329
<212> TYPE: PRT
<213> ORGANISM: Mycobacterium tuberculosis

<400> SEQUENCE: 26

Val Ser Ala Ser Pro Leu Lys Val Ala Val Thr Gly Ala Ala Gly Gln
1               5                   10                  15

Ile Gly Tyr Ser Leu Leu Phe Arg Leu Ala Ser Gly Ser Leu Leu Gly
                20                  25                  30

Pro Asp Arg Pro Ile Glu Leu Arg Leu Leu Glu Ile Glu Pro Ala Leu
            35                  40                  45

Gln Ala Leu Glu Gly Val Val Met Glu Leu Asp Asp Cys Ala Phe Pro
    50                  55                  60

Leu Leu Ser Gly Val Glu Ile Gly Ser Asp Pro Gln Lys Ile Phe Asp
65                  70                  75                  80

Gly Val Ser Leu Ala Leu Leu Val Gly Ala Arg Pro Arg Gly Ala Gly
                85                  90                  95

Met Glu Arg Ser Asp Leu Leu Glu Ala Asn Gly Ala Ile Phe Thr Ala
            100                 105                 110

Gln Gly Lys Ala Leu Asn Ala Val Ala Ala Asp Asp Val Arg Val Gly
        115                 120                 125

Val Thr Gly Asn Pro Ala Asn Thr Asn Ala Leu Ile Ala Met Thr Asn
    130                 135                 140

Ala Pro Asp Ile Pro Arg Glu Arg Phe Ser Ala Leu Thr Arg Leu Asp
145                 150                 155                 160

His Asn Arg Ala Ile Ser Gln Leu Ala Ala Lys Thr Gly Ala Ala Val
                165                 170                 175

Thr Asp Ile Lys Lys Met Thr Ile Trp Gly Asn His Ser Ala Thr Gln
            180                 185                 190

Tyr Pro Asp Leu Phe His Ala Glu Val Ala Gly Lys Asn Ala Ala Glu
        195                 200                 205

Val Val Asn Asp Gln Ala Trp Ile Glu Asp Glu Phe Ile Pro Thr Val
    210                 215                 220

Ala Lys Arg Gly Ala Ala Ile Ile Asp Ala Arg Gly Ala Ser Ser Ala
225                 230                 235                 240

```
Ala Ser Ala Ala Ser Ala Thr Ile Asp Ala Ala Arg Asp Trp Leu Leu
                245                 250                 255

Gly Thr Pro Ala Asp Asp Trp Val Ser Met Ala Val Val Ser Asp Gly
            260                 265                 270

Ser Tyr Gly Val Pro Glu Gly Leu Ile Ser Ser Phe Pro Val Thr Thr
            275                 280                 285

Lys Gly Gly Asn Trp Thr Ile Val Ser Gly Leu Glu Ile Asp Glu Phe
        290                 295                 300

Ser Arg Gly Arg Ile Asp Lys Ser Thr Ala Glu Leu Ala Asp Glu Arg
305                 310                 315                 320

Ser Ala Val Thr Glu Leu Gly Leu Ile
                325

<210> SEQ ID NO 27
<211> LENGTH: 205
<212> TYPE: PRT
<213> ORGANISM: Mycobacterium tuberculosis

<400> SEQUENCE: 27

Met Thr Gly Pro Thr Thr Asp Ala Asp Ala Ala Val Pro Arg Arg Val
1               5                   10                  15

Leu Ile Ala Glu Asp Glu Ala Leu Ile Arg Met Asp Leu Ala Glu Met
                20                  25                  30

Leu Arg Glu Glu Gly Tyr Glu Ile Val Gly Glu Ala Gly Asp Gly Gln
            35                  40                  45

Glu Ala Val Glu Leu Ala Glu Leu His Lys Pro Asp Leu Val Ile Met
    50                  55                  60

Asp Val Lys Met Pro Arg Arg Asp Gly Ile Asp Ala Ala Ser Glu Ile
65                  70                  75                  80

Ala Ser Lys Arg Ile Ala Pro Ile Val Val Leu Thr Ala Phe Ser Gln
                85                  90                  95

Arg Asp Leu Val Glu Arg Ala Arg Asp Ala Gly Ala Met Ala Tyr Leu
            100                 105                 110

Val Lys Pro Phe Ser Ile Ser Asp Leu Ile Pro Ala Ile Glu Leu Ala
        115                 120                 125

Val Ser Arg Phe Arg Glu Ile Thr Ala Leu Glu Gly Glu Val Ala Thr
    130                 135                 140

Leu Ser Glu Arg Leu Glu Thr Arg Lys Leu Val Glu Arg Ala Lys Gly
145                 150                 155                 160

Leu Leu Gln Thr Lys His Gly Met Thr Glu Pro Asp Ala Phe Lys Trp
                165                 170                 175

Ile Gln Arg Ala Ala Met Asp Arg Arg Thr Thr Met Lys Arg Val Ala
            180                 185                 190

Glu Val Val Leu Glu Thr Leu Gly Thr Pro Lys Asp Thr
        195                 200                 205

<210> SEQ ID NO 28
<211> LENGTH: 181
<212> TYPE: PRT
<213> ORGANISM: Mycobacterium tuberculosis

<400> SEQUENCE: 28

Val Arg Val Leu Leu Leu Gly Pro Pro Gly Ala Gly Lys Gly Thr Gln
1               5                   10                  15

Ala Val Lys Leu Ala Glu Lys Leu Gly Ile Pro Gln Ile Ser Thr Gly
                20                  25                  30
```

```
Glu Leu Phe Arg Arg Asn Ile Glu Glu Gly Thr Lys Leu Gly Val Glu
            35                  40                  45

Ala Lys Arg Tyr Leu Asp Ala Gly Asp Leu Val Pro Ser Asp Leu Thr
 50                      55                  60

Asn Glu Leu Val Asp Asp Arg Leu Asn Asn Pro Asp Ala Ala Asn Gly
 65                  70                  75                  80

Phe Ile Leu Asp Gly Tyr Pro Arg Ser Val Glu Gln Ala Lys Ala Leu
                 85                  90                  95

His Glu Met Leu Glu Arg Arg Gly Thr Asp Ile Asp Ala Val Leu Glu
            100                 105                 110

Phe Arg Val Ser Glu Glu Val Leu Glu Arg Leu Lys Gly Arg Gly
            115                 120                 125

Arg Ala Asp Asp Thr Asp Asp Val Ile Leu Asn Arg Met Lys Val Tyr
130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180

<210> SEQ ID NO 29
<211> LENGTH: 200
<212> TYPE: PRT
<213> ORGANISM: Mycobacterium tuberculosis

<400> SEQUENCE: 29

Val Ser Gln Val Thr Asp Met Arg Ser Asn Ser Gln Gly Leu Ser Leu
 1               5                  10                  15

Thr Asp Ser Val Tyr Glu Arg Leu Leu Ser Glu Arg Ile Ile Phe Leu
                20                  25                  30

Gly Ser Glu Val Asn Asp Glu Ile Ala Asn Arg Leu Cys Ala Gln Ile
            35                  40                  45

Leu Leu Leu Ala Ala Glu Asp Ala Ser Lys Asp Ile Ser Leu Tyr Ile
 50                      55                  60

Asn Ser Pro Gly Gly Ser Ile Ser Ala Gly Met Ala Ile Tyr Asp Thr
 65                  70                  75                  80

Met Val Leu Ala Pro Cys Asp Ile Ala Thr Tyr Ala Met Gly Met Ala
                 85                  90                  95

Ala Ser Met Gly Glu Phe Leu Leu Ala Ala Gly Thr Lys Gly Lys Arg
            100                 105                 110

Tyr Ala Leu Pro His Ala Arg Ile Leu Met His Gln Pro Leu Gly Gly
            115                 120                 125

Val Thr Gly Ser Ala Ala Asp Ile Ala Ile Gln Ala Glu Gln Phe Ala
130                 135                 140

Val Ile Lys Lys Glu Met Phe Arg Leu Asn Ala Glu Phe Thr Gly Gln
145                 150                 155                 160

Pro Ile Glu Arg Ile Glu Ala Asp Ser Asp Arg Asp Arg Trp Phe Thr
                165                 170                 175

Ala Ala Glu Ala Leu Glu Tyr Gly Phe Val Asp His Ile Ile Thr Arg
            180                 185                 190

Ala His Val Asn Gly Glu Ala Gln
            195                 200

<210> SEQ ID NO 30
```

<211> LENGTH: 303
<212> TYPE: PRT
<213> ORGANISM: Mycobacterium tuberculosis

<400> SEQUENCE: 30

```
Met Thr His Met Ser Ile Phe Leu Ser Arg Asp Asn Lys Val Ile Val
1               5                   10                  15

Gln Gly Ile Thr Gly Ser Glu Ala Thr Val His Thr Ala Arg Met Leu
            20                  25                  30

Arg Ala Gly Thr Gln Ile Val Gly Gly Val Asn Ala Arg Lys Ala Gly
        35                  40                  45

Thr Thr Val Thr His Glu Asp Lys Gly Gly Arg Leu Ile Lys Leu Pro
50                  55                  60

Val Phe Gly Ser Val Ala Glu Ala Met Glu Lys Thr Gly Ala Asp Val
65                  70                  75                  80

Ser Ile Ile Phe Val Pro Pro Thr Phe Ala Lys Asp Ala Ile Ile Glu
                85                  90                  95

Ala Ile Asp Ala Glu Ile Pro Leu Leu Val Val Ile Thr Glu Gly Ile
            100                 105                 110

Pro Val Gln Asp Thr Ala Tyr Ala Trp Ala Tyr Asn Leu Glu Ala Gly
        115                 120                 125

His Lys Thr Arg Ile Ile Gly Pro Asn Cys Pro Gly Ile Ile Ser Pro
    130                 135                 140

Gly Gln Ser Leu Ala Gly Ile Thr Pro Ala Asn Ile Thr Gly Pro Gly
145                 150                 155                 160

Pro Ile Gly Leu Val Ser Lys Ser Gly Thr Leu Thr Tyr Gln Met Met
                165                 170                 175

Phe Glu Leu Arg Asp Leu Gly Phe Ser Thr Ala Ile Gly Ile Gly Gly
            180                 185                 190

Asp Pro Val Ile Gly Thr Thr His Ile Asp Ala Ile Glu Ala Phe Glu
        195                 200                 205

Arg Asp Pro Asp Thr Lys Leu Ile Val Met Ile Gly Glu Ile Gly Gly
    210                 215                 220

Asp Ala Glu Glu Arg Ala Ala Asp Phe Ile Lys Thr Asn Val Ser Lys
225                 230                 235                 240

Pro Val Val Gly Tyr Val Ala Gly Phe Thr Ala Pro Glu Gly Lys Thr
                245                 250                 255

Met Gly His Ala Gly Ala Ile Val Ser Gly Ser Gly Thr Ala Ala
            260                 265                 270

Ala Lys Gln Glu Ala Leu Glu Ala Ala Gly Val Lys Val Gly Lys Thr
        275                 280                 285

Pro Ser Ala Thr Ala Ala Leu Ala Arg Glu Ile Leu Leu Ser Leu
    290                 295                 300
```

<210> SEQ ID NO 31
<211> LENGTH: 295
<212> TYPE: PRT
<213> ORGANISM: Mycobacterium tuberculosis

<400> SEQUENCE: 31

```
Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

Ser Pro Ala Leu Tyr Leu Leu Asp Gly Leu Arg Ala Gln Asp Asp Phe
        35                  40                  45
```

-continued

```
Ser Gly Trp Asp Ile Asn Thr Pro Ala Phe Glu Trp Tyr Asp Gln Ser
     50                  55                  60
Gly Leu Ser Val Val Met Pro Val Gly Gly Gln Ser Ser Phe Tyr Ser
65                   70                  75                  80
Asp Trp Tyr Gln Pro Ala Cys Gly Lys Ala Gly Cys Gln Thr Tyr Lys
                 85                  90                  95
Trp Glu Thr Phe Leu Thr Ser Glu Leu Pro Gly Trp Leu Gln Ala Asn
                100                 105                 110
Arg His Val Lys Pro Thr Gly Ser Ala Val Val Gly Leu Ser Met Ala
            115                 120                 125
Ala Ser Ser Ala Leu Thr Leu Ala Ile Tyr His Pro Gln Gln Phe Val
        130                 135                 140
Tyr Ala Gly Ala Met Ser Gly Leu Leu Asp Pro Ser Gln Ala Met Gly
145                 150                 155                 160
Pro Thr Leu Ile Gly Leu Ala Met Gly Asp Ala Gly Gly Tyr Lys Ala
                165                 170                 175
Ser Asp Met Trp Gly Pro Lys Glu Asp Pro Ala Trp Gln Arg Asn Asp
                180                 185                 190
Pro Leu Leu Asn Val Gly Lys Leu Ile Ala Asn Asn Thr Arg Val Trp
            195                 200                 205
Val Tyr Cys Gly Asn Gly Lys Pro Ser Asp Leu Gly Gly Asn Asn Leu
        210                 215                 220
Pro Ala Lys Phe Leu Glu Gly Phe Val Arg Thr Ser Asn Ile Lys Phe
225                 230                 235                 240
Gln Asp Ala Tyr Asn Ala Gly Gly His Asn Gly Val Phe Asp Phe
                245                 250                 255
Pro Asp Ser Gly Thr His Ser Trp Glu Tyr Trp Gly Ala Gln Leu Asn
                260                 265                 270
Ala Met Lys Pro Asp Leu Gln Arg Ala Leu Gly Ala Thr Pro Asn Thr
            275                 280                 285
Gly Pro Ala Pro Gln Gly Ala
    290                 295
```

MID-LIFE VACCINE AND METHODS FOR BOOSTING ANTI-MYCOBACTERIAL IMMUNITY

This Application was filed under 35 U.S.C. § 371 based on international application Ser. No. PCT/US01/21717 (filed 10 Jul. 2001) and claims priority from U.S. Provisional Application Ser. No. 60//217,646, filed 10 Jul. 2000.

This invention was funded in part by grants AI045707, AI075320 and AG006946 from the National Institutes of Health, which provides to the United States government certain rights in this invention.

BACKGROUND OF THE INVENTION

1. Field of the Invention

The present invention in the fields of microbiology, immunology and medicine is directed to vaccine compositions and methods for preventing or treating mycobacterial diseases that are particularly suited to immunize a subject in mid-life who has been vaccinated neonatally or in early childhood with BCG and in whom protective immunity has waned. Thirty proteins from *Mycobacterium tuberculosis* are disclosed as having the desired immunogenicity and T cell stimulatory activity for such use. A preferred protein is Ag85A, the secreted product (SEQ ID NO:31) of the Rv3084c gene.

2. Description of the Background Art

Current epidemiologic data indicates that disease caused by the facultative intracellular bacterial parasite *Mycobacterium tuberculosis* (*M. tuberculosis* or "Mtb") remains a serious global problem with around 8 million new cases per year, and with recent disturbing evidence that the death rate may be increasing (B. R. Bloom et al., *Science* 257:1055-64 (1992); M. C. Raviglione et al., *Lancet* 350:624-9 (1997); P. J. Dolin et al., *Bull World Health Organ* 72, 213-20 (1994); D. E. Snider, Jr., et al., *N Engl J Med* 338:1689-90 (1998).

For several decades the *M. bovis*-derived bacillus Calmette Guerin (BCG) has been the only widely used vaccine for tuberculosis ("TB"). BCG organisms, a strain of *M. bovis*, has been the only widely used vaccine for TB. However, accumulating data from clinical trials and subsequent meta-analysis (G. A. Colditz, et al., *JAMA* 271:698-702 (1994); J. A. Sterne et al., *Int J Tuberc Lung Dis* 2:200-7 (1998)) are revealing its general ineffectiveness in adults. It is noteworthy that adults vaccinated with BCG as young children become relatively unprotected. As a result many investigators are seeking to develop a new TB vaccine (I. M. Orme, *Adv Vet Med* 41:135-43 (1999); 1. M. Orme, *Infect Dis Clin North Am* 13:169-85, vii-viii (1999)); virtually all efforts are directed towards discovering new candidate vaccines that can be used in either or both prophylactic or immunotherapeutic modes (P. Andersen, *Scand J Immunol* 45:115-31 (1997). M. A. Horwitz et al., *Proc Natl Acad Sci USA* 92, 1530-4 (1995); D. B. Lowrie, et al., *Nature* 400: 269-71 (1999)).

The mechanism underlying the gradual loss of effectiveness of BCG as the neonatally inoculated subject reaches 10-15 years of age is poorly understood. One possibility is that immunological memory generated by BCG has disappeared so that the subject is now the functional equivalent of a naive host that should be vaccinated with a new candidate vaccine that is designed to induce primary immunity as does BCG. An alternate possibility is slowly declining immunological memory can be re-induced by boosting with a candidate antigen that is specifically recognized by host memory cells (primarily T cells). The present invention is directed to the latter possibility and indeed discloses a number of Mtb antigens that can restimulate T cell memory and protective immunity.

The recent elucidation of the entire genome sequence of *M. tuberculosis* strain H37Rv (Cole, S. T. et al., *Nature* 1998, 393:537-544) is one of the most significant advancements to occur in tuberculosis research over the last decade and this data is now the backbone for several facets of tuberculosis research, including detailed analyses of the proteome of *M. tuberculosis*. Several laboratories have published two-dimensional ("2-D") protein maps of the subcellular-fractions of *M. tuberculosis* (Jungblut, P R. et al., *Mol. Microbiol.* 1999, 33:1103-1117; Sonnenberg, M G and Belisle, J T, *Infect. Immun.* 1997, 65:4515-4524). Others have applied this technology to evaluate the proteins produced by *Mycobacterium* spp. during intracellular growth (Sturgill-Koszycki, S et al. *Electrophoresis* 1997, 18:2558-2565; Bai-Yu, L. et al., *J. Clin. Invest.* 1995, 96: 245-2496). Proteomics is also a facile approach to identifying immunodominant molecules. Through the use of 2-D PAGE and Western blot analysis, Samanich et al., *J. Infect. Dis.* 1998, 178, 1534-1538, recently defined 26 proteins of *M. tuberculosis* that reacted with antibodies of tuberculosis patients, and three of theses were determined to have potent serodiagnostic potential. See also, Laal et al., U.S. Pat. No. 6,245,331. However such an approach has not been applied on a large scale to the molecular identification of the T cell antigens of *M. tuberculosis*.

T cells mediate the protective immune response to an *M. tuberculosis* infection (Orme, I M et al., *J. Infect. Dis.* 1993, 167:1481-1497), and elucidation of the T cell antigens has been a driving force in the identification of *M. tuberculosis* proteins. However, many of the proteins assessed for T cell reactivity were selected because they were abundant, easily purified or reactive to existing monoclonal antibodies (mAbs). Realizing that the study of T cell antigens required a systematic approach, Andersen and Heron, *J. Immun. Methods* 1993. 16, 29-39, developed a whole-gel elutor to systematically fractionate short-term *M. tuberculosis* culture filtrate proteins (CFPs) by size. This group and others have used this technique to identify T cell antigens and develop 1-D patterns of proteins inducing T cell reactivity (Boesen, H et al., *Infect. Immun.* 1995, 63:1491-1497; Roberts, A D et al., *Immunol.* 1995, 85:502-508). Andersen's group (Weldingh, K et al., *FEMS Immunol. Med. Microbiol.* 1999, 23:159-164) recently coupled this technique with preparative IEF to provide greater resolution. However, this work was focused on characterization of a small number of proteins. Similarly, Gulle et al., *Vet. Immunol. Immunopath.* 1995, 48:183-190) performed T cell proliferative studies of *M. bovis* BCG proteins that were electroeluted from 2-D polyacrylamide gels. Although this work revealed a detailed 2-D pattern of potential T cell antigens, those proteins found to be immunogenic were not identified. Moreover this approach had several inherent limitations such as, the amount of protein obtained by elution from a single gel was insufficient for multiple analyses, and the concentration of individual proteins tested varied.

Several laboratories, including the present inventors', have shown that proteins found in Mtb culture filtrates are highly immunogenic and have promise as candidate vaccines (Orme, supra). One member of this pool, disclosed herein to be a preferred boosting antigen, is the mycolyl transferase A enzyme also termed Ag85A (J. T. Belisle, et al., *Science* 276:1420-2 (1997)) (and also known as FbpA, encoded by the Mtb gene Rv3804c (available in GenBank).

The present inventors and their colleagues demonstrated that the majority of CD4+ T cells accumulating in the lungs of immune mice after challenge infection recognize this antigen (A. M. Cooper et al., *Tuber Lung Dis* 78:67-73 (1997)).

Mice infected with *M. tuberculosis* generate T cells that recognize the Ag85 protein. As a consequence, investigators have attempted to use Ag85 protein as a primary vaccine. It appears that no one has shown any vaccine or antigen preparation that approaches the protection conferred by the "gold standard" vaccine, BCG.

Horwitz MA et al., 1995, supra, claimed that Ag85 protein protected guinea pigs against aerosol TB. This study was said by the authors to demonstrate that immunization with the Mtb 30-kDa major secretory protein (Ag85A), alone or in combination with other abundant extracellular Mtb proteins induced strong cell-mediated immune responses and substantial protective immunity against aerosal challenge with virulent Mtb *bacilli* in the highly susceptible guinea pig model of pulmonary tuberculosis. Protection was manifested by decreased morbidity (including decreased weight loss and mortality), and decreased growth of Mtb in the lungs and spleens compared with sham-immunized controls. The authors concluded that purified major extracellular proteins of Mtb are candidate components of a subunit vaccine against TB. It is noteworthy that Ag85 was given mixed with other proteins, and an adjuvant that cannot be used in humans. Moreover, the experiment had no positive control, it was halted before the negative control animals died. This paper has been widely criticized for its lack od proper scientific methodology.

In contrast, the present inventors conducted a controlled, uncontaminated test of Ag85 as a primary vaccine in guinea pigs and found no reduction in lung bacterial load.

U.S. Pat. No. 5,736,524 discloses the use of primary DNA vaccines that encode Ag85. However, experience since this document became public has shown that the vaccines disclosed therein are even less effective than BCG.

Moreover, booster inoculation of BCG has proven ineffective. Thus, people who were neonatally vaccinated with BCG are at risk for TB as their T cell reactivity and antibody titers decline over time after primary vaccination.

While there is a desperate need to develop new TB vaccines to deal with the global emergency in general, in more advanced countries TB continues to be relatively more common in the elderly (W. W. Stead et al., *Annu Rev Med* 42: 267-726 (1991); W. W. Stead, *Int J Tuberc Lung Dis* 2: S64-70 (1998)). In the United States, for instance, people over the age of 65 have for some time now represented the fastest growing segment of the overall population (US Census Bureau. Worldwide Web page having the URL: .census.gov/socdemo/www/agebrief.html). While primary TB sometimes occurs in these individuals, the majority of cases are thought to be due to reactivation of latent disease acquired many decades earlier (Steadl, 1998, supra). h view of this, the vaccine strategy disclosed herein is applicable for preventing reactivation TB in the elderly.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have discovered, through the use of 2-D liquid phase electrophoresis (LPE) (Davidsson, P et al., *Biochim. Biophys. Acta* 1999, 1473:391-399) coupled with an in vitro interferon-γ (IFNγ) assay (Orme, IM et al., *J. Immunol.* 1993,151:518-52516), and liquid chromatograph-mass spectromeltry (LC-MS) T cell immunogens in the culture filtrate and cytosol fractions of *M. tuberculosis*. In total, 31 individual proteins that stimulated a strong IFNγ response from T cells of *M. tuberculosis* infected mice were identified. This procedure permitted recovery of significant total amounts olf proteins and had the advantage of rapidly and accurately identifying the proteins that can serve as T cell immunogens. See, also: Covert, B A et al., *Proteomics,* 2001, 1:574-586, which is incorporated by reference in its entirety.

The present inventors discovered that immunization with an immunogenic secreted protein of Mtb, as exemplified by Ag85A, boosted the immune response, and thus the state of existing immunological memory, in recipients that had been previously vaccinated with BCG See, also: Brooks, J. V. et al., *Infec. Immun.,* 2001, 69:2714-2717, which is incorporated by reference in its entirety.

Studies performed in mice showed that midlife boosting of BCG-vaccinated animals restored resistance to challenge with virulent *M. tuberculosis* organisms when the subjects were elderly. Such a state of resistance was not seen in animals that had simply been given BCG early in life.

The present invention provides a vaccine composition useful for boosting the immune response to Mtb in a mammal which has been vaccinated neonatally or early in life with BCG, to increase the resistance of the mammal to Mtb infection, the composition comprising one or more, (or, in another embodiment, two or more, or in yet another embodiment, three or more) purified Mtb proteins, or homologues or functional derivatives of the proteins, which protein, homologue or functional derivative is characterized in that that it:

(a) stimulates significant interferon-γ secretion by T lymphocytes of a mammal which has been immunized with Mtb antigens; and/or (b) when administered to a mammalian subject at an age when immunity induced by the BCG vaccination is waning, it significantly increases the resistance of the subject to Mtb infection.

Preferably in the above vaccine composition, the purified Mtb proteins are selected from the group consisting of the product of the Mtb gene Rv3804c, Rv1886c, Rv0029c, Rv1860, Rv0934, Rv0577, Rv1827, Rv3841, Rv1932, Rv1352, Rv3418c, Rv3875, Rv1810, Rv1980c, Rv0350, Rv3044, Rv0054, Rv0652, Rv3029c, Rv3028c, Rv2428, Rv0440, Rv2031c, Rv2626c, Rv1211, Rv1240, Rv1626, Rv0733, Rv2461c, and Rv0952.

Alternatively, in the vaccine composition, the purified proteins are selected from the group consisting of SEQ ID NO:1, SEQ: ID NO:2, SEQ: ID NO:3, SEQ: ID NO:4, SEQ: ID NO:5, SEQ: ID NO:6, SEQ: ID NO:7, SEQ: ID NO:8, SEQ: ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30 and SEQ ID NO:31, wherein, when the protein is an Mtb secreted protein, the sequence is the truncated sequence of the above sequences from which the signal sequence has been removed.

In another embodiment of the vaccine composition, the proteins are selected from the group consisting of SEQ ID NO:6; SEQ ID NO:8; SEQ ID NO:10; SEQ ID NO:13; SEQ ID NO:16; SEQ ID NO:17; SEQ ID NO:18; SEQ ID NO:19; SEQ ID NO:20; SEQ ID NO:21; SEQ ID NO:24; SEQ ID NO:25; SEQ ID NO:26; SEQ ID NO:27; SEQ ID NO:28; SEQ ID NO:29 and SEQ ID NO:30.

In yet another embodiment of the vaccine composition, the proteins are selected from the group consisting of SEQ ID NO:6; SEQ ID NO:7; SEQ ID NO:10; SEQ ID NO:13; SEQ ID NO:24; SEQ ID NO:25 and SEQ ID NO:27.

A preferred vaccine composition includes Ag85A (SEQ ID NO:31).

The above vaccine composition preferably further comprises an adjuvant or an immunostimulatory protein different from the immunogenic Mtb proteins. The immunostimulatory protein may be a cytokine, e.g., interleukin 2 or GM-CSF.

The adjuvant is preferably one or more of: (a) ISAF-1 (5% squalene, 2.5% pluronic L121, 0.2% Tween 80) in phosphate-buffered solution with 0.4 mg of threonyl-muramyl dipeptide; (b) Amphigen®; (c) Alhydrogel®; (d) a mixture of Amphigen® and Alhydrogel® (e) QS-21; and (f) monophosphoryl lipid A adjuvant. A preferred adjuvant is monophosphoryl lipid A adjuvant solubilized in 0.02% triethanolamine and a preferred cytokine is rIL-2.

Also provided herein is a method for boosting the immune response to Mycobacterium tuberculosis (Mtb) in a mammal which has been vaccinated neonatally or early in life with BCG, to increase the resistance of the mammal to Mtb infection, the method comprising administering to a mammal in need of the boosting, an immunogenically effective amount of an Mtb immunogenic protein vaccine composition as described above.

Preferably the mammal is a human. The administering is preferably performed between about 1 and about 10 years after the BCG vaccination. In preferred embodiments, the administering is performed when the human is at least about 10 years of age, or at least about 15 years of age, or at least about 20 years of age.

In one embodiment of the above method, the vaccine composition includes a single Mtb protein (or homologue or functional derivative thereof. A preferred protein is Ag85A (SEQ ID NO:31).

BRIEF DESCRIPTION OF THE DRAWINGS

FIGS. 1 and 3 show responses to the 2-D LPE fractions of the CFPs, and FIGS. 2 and 4 are the responses to the 2-D LPE. fractions of the cytosolic proteins. Each bar represents a T cell response to a single 2-D LPE fraction. These responses were calculated as the amount (ng/mL) of IFN-γ produced by cells from infected mice minus the IFNγ produced by cells from uninfected mice tested with the same 2-D LPE fraction. Each vertical data bar progressing in a row along the "kDa" axis (some showing different hatching patterns), represents a molecular weight range of 5 kDa. All 2-D LPE fractions were placed in a molecular weight range of 10-15, 15-20, 20-25, 25-30, 30-35, 35-40, 40-45, 45-45, 50-55, 55-60, 60-65, 65-70, 70-75, 75-80, 80-85, 85-90, 90-95, 95-100, 100-105, 105-110, 110-115, or 115-120 kDa.

Figure 1:
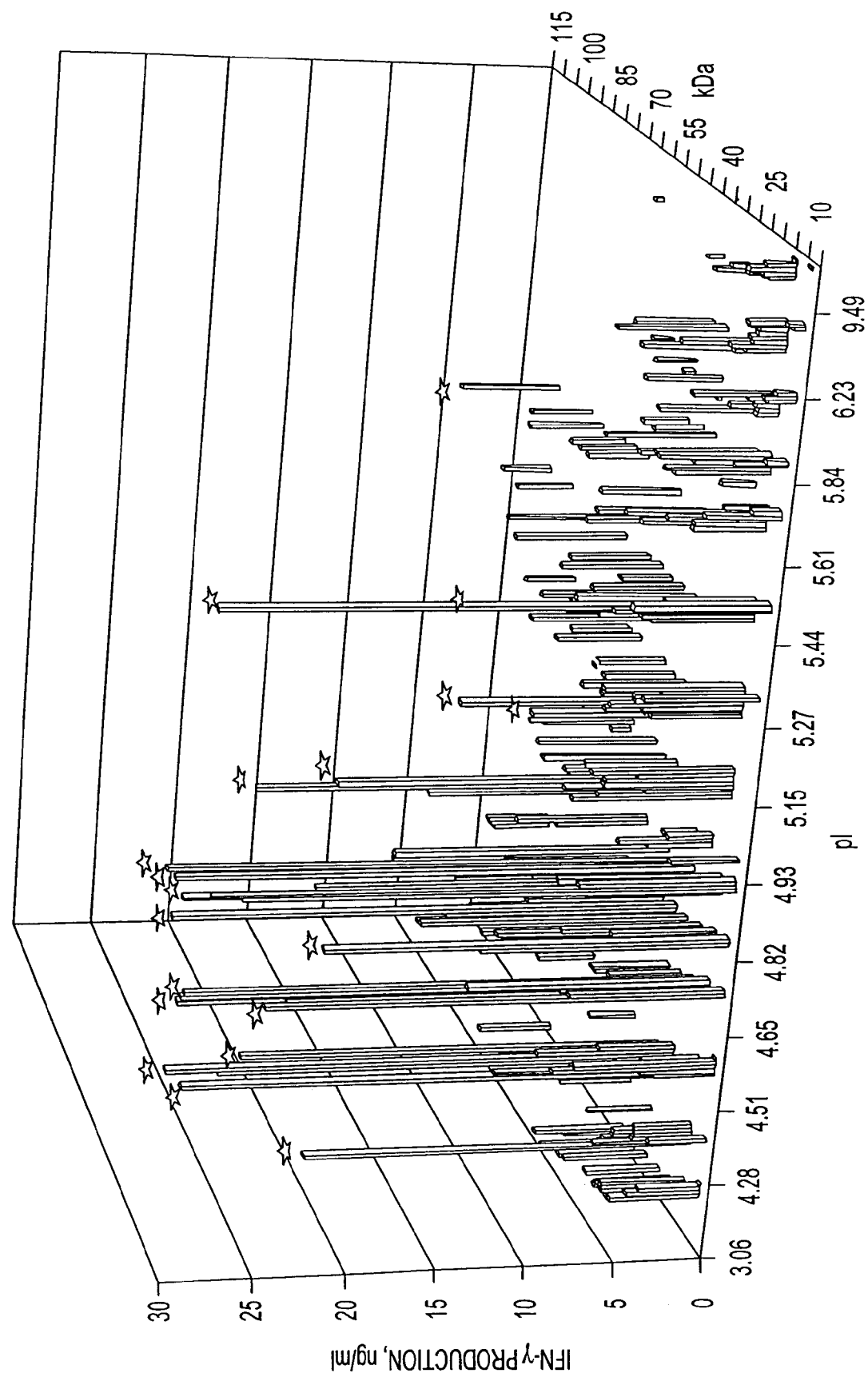
FIGS. 1-4 show IFNγ responses of spleen lymphocytes harvested from C57B1/6 mice at 10 days (FIGS. 1 and 2) and 40 days (FIGS. 3 and 4) post infection with *M. tuberculosis* H37Rv.

Plate A: Lung adjacent to a bronchiole (arrowhead) from a mouse from the BCG vaccination group. Alveolar septa containing epithelioid macrophages and infiltrates of neutrophils, often forming small aggregates, were evident (arrows).

Plate B: Lung adjacent to a bronchiole (arrowhead) from a mouse from the BCG/Ag85 vaccination group. The alveolar septa showed influx by epithelioid macrophages, whereas neutrophils were scattered and rare (arrows).

Plate C: Higher magnification of lung from a mouse from the BCG vaccination group. Arrows depict an aggregate or pocket of neutrophils within an alveolar septum.

Plate D: Higher magnification of lung from a mouse from the BCG/Ag85 vaccination group. The septa were thickened by an influx of macrophages. Neutrophils were rare; the arrow indicates an solitary neutrophil.

DESCRIPTION OF THE PREFERRED EMBODIMENTS

This invention represents the first discovery an animal immunized when young with BCG can be boosted in mid-life with an antigen that is strongly recognized by the memory T lymphocytes, resulting in the expression of immunity in the elderly animal that is equivalent in potency to that seen in young mice vaccinated with BCG (and challenged soon thereafter).

While these observations were in mice, the present invention provides compositions and methods to achieve a similar effect in humans that had been previously vaccinated with BCG.

Another advantage of the present approach is considerable simplification of testing new vaccines in the field, particularly in the third world. Although most vaccine research focuses on new prophylactic measures to replace BCG vaccination altogether, the fact remains that most newborn children, especially in regions where TB is prevalent, are given BCG vaccination almost immediately after birth.

In fact it is not known if most vaccine strategies under development will actually work if given to people who haw: an existing state of immunity, measured in any of a number of ways, to Mtb.

The present approach offers the advantage that it does not ignore the fact of previous BCG vaccination like the approaches of others that attempt to design vaccines to induce a "new" state of primary immunity. Rather, the present invention is specifically targeted to subjects who carry a state of immunological memory by using any one or a combination of purified protein antigens (or immunogenic epitopes thereof) that are recognized by T cells, preferably, CD4+ memory T cells, even if these T cells exist in a milieu (or pool) or memory cells that is gradually waning over time. As described in Example I, below, Ag85A is a preferred example of such an antigen.

The present invention is superior to the strategy of using an immunogenic protein or proteins, such as Ag85A, directly as a primary vaccine. It has been shown that some degree of primary immunity can certainly be generated against such proteins, e.g., Ag85, ESAT-6, 45 kDa, etc., in mice (I. M. Orme, *Infect Dis Clin North Am* 13, 169-85, vii-viii (1999); S. H. Kaufmann et al., *Chem Immunol* 70:21-59 (1998)). However, such a level of immunity does not usually exceed that conferred by BCG, and more importantly, there is no evidence to date of a sustained, long-lived state of immunological memory established by primary immunization with individual proteins or mixtures of such proteins.

The present inventors and their colleagues have found that immunization with Ag85A can induce modest levels of protection in mice challenged 30 days later (S. L. Baldwin, et al., *Infect Immun* 66:2951-2959 (1998)). In guinea pigs, such immunization had no effect on the bacterial load, although modest "clinical" benefits, measured as lymphocytic granuloma formation in lungs coupled with reasonably long term survival were observed (unpublished observations). This however did not compare to BCG vaccination, which resulted in 2-3 log reduction in a bacterial load and animals living for most of their expected lifespan. A much better single protein immunization result was obtained if the Ag85A was delivered in the form of a DNA vaccine (K. Huygen et al., *Nature Med* 8: 893-898 (1996)). Again, however, this strategy did not appreciably reduce the bacterial load in the sensitive guinea pig model.

It is unknown why Ag85A cannot prime animals to the degree achieved by BCG. This underscores the current inability in the art to induce a strong $T_H1$-mediated primary and long-lived memory response to non-living vaccines compared to levels attained using BCG.

One limitation is the paucity of vaccine adjuvants. The present inventors and others have worked with relatively mild adjuvants such as monophosphoryl lipid A (MPL) and DDA primarily because they are considered safe for use in humans. However, these adjuvants alone are believed to be insufficient to induce long lived $T_H1$-mediated immunity. However, according to the present invention, such adjuvants are sufficiently effective for boosting of a response in a BCG-vaccinated subject using an isolated protein antigen (or mixture thereof) when the subject already has sufficient antigen-specific $T_H1$ cells; as part of a state of specific immunological memory as a result of BCG exposure early in life.

Recombinant *M. Tuberculosis* Proteins

Purified immunogenic Mtb proteins described herein may be produced using recombinant methods. Conventional bacterial expression systems utilize Gram negative bacteria such as *E. coli* or *Salmonella* species. However, it is believed that such systems may not be ideally suited for production of Mtb antigens (Burlein, J. E., In: *Tuberculosis: Pathogenesis, Protection and Control*, B. Bloom, ed., Amer. Soc. Microbiol., Washington, D.C., 1994, pp. 239-252). Rather, it is preferred to utilize homologous mycobacterial hosts for recombinant production of Mtb antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D. A. et al., 1996, *Mol. Microbiol.* 22:583-592) and the other of non mycobacterial genes, such as HIV-1 genes (Winter, N. et al., 1992, *Vaccines 92*, Cold Spring Harbor Press, pp. 373-378) expressed in mycobacterial hosts are cited herein as an example of the state of the art. The foregoing three references are hereby incorporated by reference in their entirety.

General Recombinant DNA Methods

Basic texts disclosing general methods of molecular biology, all of which are incorporated by reference, include: Sambrook, J. et al., *Molecular Cloning: A Laboratory Manual*, 2$^{nd}$ Edition, Cold Spring Harbor Press, Cold Spring Harbor, N.Y., 1989; Ausubel, F. M. et al. *Current Protocols in Molecular Biology*, Vol. 2, Wiley-Interscience, New York, (current edition); Kriegler, *Gene Transfer and Expression: A Laboratory Manual* (1990); Glover, D. M., ed, *DNA Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J. D. et al., *Recombinant DNA*, 2$^{nd}$ Ed., Scientific American Books, New York, 1992; and Old, R W et al., *Principles of Gene Manipulatxion: An Introduction to Genetic Engineering*, 2$^{nd}$ Ed., University of California Press, Berkeley, Calif. (1981).

Unless otherwise indicated, a particular nucleic acid sequence additionally encompasses conservative substitution variants thereof (e.g., degenerate codon substitutions) and a complementary sequence. The term "nucleic acid" is synonymous with "polynucleotide" and is intended to include a gene, cDNA molecule, an mRNA molecule, as well as a fragment of any of these such as an oligonucleotide, and further, equivalents thereof (explained more fully below). Sizes of nucleic acids stated either as kilobases (kb) or base pairs (bp) are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

cDNA molecules encoding the amino acid sequence of the immunogenic Mtb protein or fragments or derivatives thereof can be synthesized by the polymerase chain reaction (PCR) (see, for example, U.S. Pat. No. 4,683,202) using primers derived the sequence of the protein which are publicly disclosed. These cDNA sequences can then be assembled into a prokaryotic expression vector and the resulting vector can be used to direct the synthesis of the polypeptide or its fragment or derivative by appropriate host cells as indicated above.

Fragment of Nucleic Acid

A fragment of the nucleic acid sequence is defined as a nucleotide sequence having fewer nucleotides than the nucleotide sequence encoding the full length immunogenic Mtb protein. This invention includes such nucleic acid fragments that encode polypeptides which retain: (1) the ability of immunogenic Mtb protein to bind to be taken up by host antigen presenting cells and be presented to T cells, preferably TH1 cells, specific for an epitope of that protein. This can be measured by an appropriate in vitro assay such as T cell proliferation or cytokine production, e.g., IFNγ; and (2) to enhance a T cell mediated memory response to Mtb that results in statistically significantly increased protection again bacterial growth in vivo.

Generally, the nucleic acid sequence encoding an immunogenic fragment of the Mtb protein comprises nucleotides horn the sequence encoding the mature protein. Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

A culture typically includes bacterial cells such as mycobacteria, appropriate growth media and other byproducts. Suitable culture media are well known in the art and exemplified herein. The immunogenic Mtb protein can be isolated from the medium (or from cell lysates) using conventional techniques for purifying proteins and peptides, including ammonium sulfate precipitation, fractionation column chromatography (e.g., ion exchange, gel filtration, affinity chromatography, etc.) and/or electrophoresis (see generally, "Enzyme Purification and Related Techniques", *Methods in Enzymology*, 22: 233-577 (1971)). Once purified, partially or to homogeneity, the recombinant proteins of the invention can be utilized in vaccine composition as described in more detail herein.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. It may be possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Once the components of the desired vectors are thus available, they can be excised and ligated using standard restriction and ligation procedures. Site-specific DNA cleavage is performed by treating with the suitable restriction enzyme (or, enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are typically performed in 15-50 ml volumes under the following standard conditions and temperatures: for example, 20 mM Tris-HCl pH 7.5, 10 mM $MgCl_2$, 10 mM DTT, 33 µg/ml BSA, 10-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 mM total ends concentration.

In vector construction employing "vector fragments", the fragment is commonly treated with bacterial alkaline phosphatase (BAP) or calf intestinal alkaline phosphatase (CLAP) in order to remove the 5' phosphate and prevent self-ligation. Digestions are conducted at pH 8 in approximately 10 mM Tris-HCl, 1 mM EDTA using BAP or CIAP at about 1 unit/mg vector at 600 for about one hour. The preparation is extracted with phenol/chloroform and ethanol precipitated. Alternatively, re-ligation can be prevented in vectors which have been double digested by additional restriction enzyme and separation of the unwanted fragments.

Promoters

A promoter region of a DNA or RNA molecule binds RNA polymerase and promotes the transcription of an "operably linked" nucleic acid sequence. As used herein, a "promoter sequence" is the sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another.

The promoter sequences of the present invention is preferably prokaryotic. Suitable promoters are repressible, or, more preferably, constitutive. Examples of suitable prokaryotic promoters include promoters capable of recognizing the T4 (Malik, S. et al., *J. Biol. Chem.* 263:1174-1181 (1984); Rosenberg, A. H. et al., *Gene* 59:191-200 (1987); Shinedling, S. et al., *J. Molec. Biol.* 195:471-480 (1987); Hu, M. et al., *Gene* 42:21-30 (1986)), T3, Sp6, and T7 (Chamberlin, M. et al., *Nature* 228:227-231 (1970); Bailey, J. N. et al., *Proc. Natl. Acad. Sci. (U.S.A)* 80:2814-2818 (1983); Davanloo, P. et al., *Proc. Natl. Acad. Sci. (U.S.A.)* 81:2035-2039 (1984)) polymerases; the $P_R$ and $P_L$ promoters of bacteriophage λ (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176-182 (1985)) and the σ-28-specific promoters of *B. subtilis* (Gilman, M. Z., et al., *Gene* 32:11-20 (1984)); the promoters of the bacteriophages of *Bacillus* (Gryczan, T. J., In: *The Molecular Biology of the Bacilli*, Academic Press, Inc., NY (1982)); *Streptomyces* promoters (Ward, J. M., et al., *Mol. Gen. Genet.* 203:468-478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277-282 (1987)); Cenatiempo, Y. (*Biochimie* 68:505-516 (1986)); Gottesman, S. (*Ann. Rev. Genet.* 18:415-442 (1984) and the general references cited above. All of the above listed references are incorporated by reference herein. Strong promoters are preferred. Examples of such preferred promoters are those which recognize the T3, SP6 and T7 polymerases, the $P_L$ promoter of bacteriophage λ, the recA promoter The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Proteins and Polypeptides

The present invention includes an "isolated" immunogenic Mtb protein. Preferably, the protein is selected from the following proteins shown in Tables 1 and 2, below (SEQ ID NO:1-SEQ ID NO:30.

A most preferred protein is Ag85A, a protein having 295 amino acids which is the secreted form of SEQ ID NO:1 and which has the sequence:

```
FSRPGLPVEY LQVPSPSMGR DIKVQFQSGG ANSPALYLLD GLRAQDDFSG (SEQ ID NO: 31)

WDINTPAFEW YDQSGLSVVM PVGGQSSFYS DWYQPACGKA GCQTYKWETF

LTSELPGWLQ ANRHVKPTGS AVVGLSMAAS SALTLAIYHP QQFVYAGAMS

GLLDPSQAMG PTLIGLAMGD AGGYKASDMW GPKEDPAWQR NDPLLNVGKL

IANNTRVWVY CGNGKPSDLG GNNLPAKFLE GFVRTSNIKF QDAYNAGGGH

NGVFDFPDSG THSWEYWGAQ LNAMKPDLQR ALGATPNTGP APQGA.
```

Also preferred as vaccine compositions are mixtures of two of more purified proteins listed in the Table 1 and 2. A more preferred mixture includes Ag85A (SEQ ID NO:31).

While full length native immunogenic Mtb proteins are described, it is to be understood that use of homologues of these proteins from other mycobacterial species and mutants thereof that possess the characteristics disclosed herein are intended within the scope of this invention.

Also included is a "functional derivative" of the immunogenic Mtb protein which includes amino acid substitution "variants," "fragments" or a "chemical derivatives" of the immunogenic Mtb protein which terms are defined below. A functional derivative retains measurable activity, preferably that of stimulating $T_H1$ cells, preferably those from a subject primed by earlier BCG vaccination, to proliferate or to secrete cytokines. Assays for $T_H1$ cytokines, preferably interferon-γ (IFNγ) (see Example I et seq.). IL-12 and IL-18 are well-known in the art and can be performed by peripheral blood T lymphocytes obtained from a subject, before, during a course of, or at various times after, booster immunization. Thus, one way to predict whether a protein, fragment or other functional derivative falls within the scope of the present claims is to test the ability of the protein, fragment or derivative to induce IFNγ production by T cells from Mtb-immunized donors, preferably human donors, most preferably having the same major histocompatibility complex (MHC) phenotype as the subject to be immunized or the prospective recipient himself. In addition to the assays described in Example I, other well-known assays for IFNγ, including Elispot assays that permit enumeration of IFNγ-secreting cells may be used.

TABLE 1

Immunodominant Secreted Mtb Proteins identified in CFP[a]

| H37Rv Gene Product | Common Names (length - aa) | SEQ ID NO: | Amino Acid Sequences[c] | | | | |
|---|---|---|---|---|---|---|---|
| Rv3804c | FbpA Ag85A 338 aa | 1 | *MQLVDRVRGA* VEYLQVPSPS FEWYDQSGLS WLQANRHVKP AMGPTLIGLA WVYCGNGKPS DSGTHSWEYW | *VTGMSRRLVV* MGRDIKVQFQ VVMPVGGQSS TGSAVVGLSM MGDAGGYKAS DLGGNNLPAK GAQLNAMKPD | *GAVGAALVSG* SGGANSPALY FYSDWYQPAC AASSALTLAI DMWGPKEDPA FLEGFVRTSN LQRALGATPN | *LVGAVGGTAT* LLDGLRAQDD GKAGCQTYKW YHPQQFVYAG WQRNDPLLNV IKFQDAYNAG TGPAPQGA | *AGA*FSRPGLP FSGWDINTPA ETFLTSELPG AMSGLLDPSQ GKLIANNTRV GGHNGVFDFP |
| Rv1886c | FbpB Ag85B 325 aa | 2 | *MTDVSRKIRA* LQVPSPSMGR YYQSGLSIVM ANRAVKPTGS PSLIGLAMGD CGNGTPNELG THSWEYWGAQ | *WGRRLMIGTA* DIKVQFQSGG PVGGQSSFYS AAIGLSMAGS AGGYKAADMW GANIPAEFLE LNAMKGDLQS | *AAVVLPGLVG* NNSPAVYLLD DWYSPACGKA SAMILAAYHP GPSSDPAWER NFVRSSNLKF SLGAG | *LAGGAATAGA* GLRAQDDYNG GCQTYKWETF QQFIYAGSLS NDPTQQIPKL QDAYNAAGGH | FSRPGLPVEY WDINTPAFEW LTSELPQWLS ALLDPSQGMG VANNTRLWVY NAVFNFPPNG |
| Rv0129c | FbpC2 Ag85C 340 aa | 3 | *MTFFEQVRRL* GLPVEYLQVP AFEEYYQSGL AWLQANKGVS EGWWPTLIGL IWVYCGNGTP PPNGTHSWPY | *RSAATTLPRR* SASMGRDIKV QFQGGGPHAV SVIMPVGGQS PTGNAAVGLS AMNDSGGYNA SDLGGDNIPA WNEQLVAMKA | *LAIAAMGAVL* QFQGGGPHAV SFYTDWYQPS MSGGSALILA NSMWGPSSDP KFLEGLTLRT DIQHVLNGAT | *VYGLVGTFGG* YLLDGLRAQD QSNGQNYTYK AYYPQQFPYA AWKRNDPMVQ NQTFRDTYAA PPAAPAAPAA | *PATAGA*FSRP DYNGWDINTP WETFLTREMP ASLSGFLNPS IPRLVANNTR DGGRNGVFNF |
| Rv1860 | ModD MPT32 325 aa | 4 | *MHQVDPNLTR* AASPPSTAAA PVIAPNAPQP PFPGQPPPVA PGTRINQETV PDAGPPQRWF APAPAPAGEV | *RKGRLAALAI* PPAPATPVAP VRIDNPVGGF NDTRIVLGRL SLDANGVSGS VVWLGTANNP APTPTTPTPQ | *AAMASASLVT* PPPAAANTPN SFALPAGWVE DQKLYASAEA ASYYEVKFSD VDKGAAKALA RTLPA | *VAVPATANA*D AQPGDPNAAP SDAAHFDYGS TDSKAAARLG PSKPNGQIWT ESIRPLVAPP | PEPAPPVPTT PPADPNAPPP ALLSKTTGDP SDMGEFYMPY GVIGSPAANA PAPAPAPAEP |
| Rv0934 | PhoS1 PstS1 374 aa | 5 | *VKIRLHTLLA* VTLAETGSTL NIGASDAYLS AAMYQGTIKT KQDPEGWGKS SFLOQASQRG IDGPAPDGYP QVHFQPLPPA | *VLTAAPLLLA* LYPLFNLWGP EGDMAAHKGL WDDPQIAALN PGFGTTVDFP LGEAQLGNSS IINYEYAIVN VVKLSDALIA | *AAG*CGSKPPS AFHERYPNVT MNIALAISAQ PGVNLPGTAV AVPGALGENG GNFLLPDAQS NRQKDAATAQ TISS | GSPETGAGAG ITAQGTGSGA QVNYNLPGVS VPLHRSDGSG NGGMVTGCAE IQAAAAGFAS TLQAFLHWAI | TVATTPASSP GIAQAAAGTV EHLKLNGKVL DTFLFTQYLS TPGCVAYIGI KTPANQAISM TDGNKASFLD |
| Rv0577 | None[d] 261 aa | 6 | MPKRSEYRQG MATLNGEAVA MMPAFDIGDA TDKPDLALAF VPNHWHVYFA IFSVLKPAPQ | TPNWVDLQTT AIAPMPPGAP GRMSFITDPT YEAVVGLTHS VDDADATAAK Q | DQSAAKKFYT EGMPPIWNTY GAAVGLWQAN SMEIAAGQNY AAAAGGQVIA | SLFGWGYDDN IAVDDVDAVV RHIGATLVNE RVLKAGDAEV EPADIPSVGR | PVPGGGGVYS DKVVPGGGQV TGTLIWNELL GGCMEPPMPG FAVLSDPQGA |
| Rv1827 | CP17 162 aa | 7 | VTDMNPDIEK LPPGSALLVV FRLENNEFNV KQGEDDGSTG | DQTSDEVTVE KRGPNAGSRF VDVGSLNGTY GP | TTSVFRADFL LLDQAITSAG VNREPVDSAV | SELDAPAQAG RHPDSDIFLD LANGDEVQIG | TESAVSGVEG DVTVSRRHAE KFRLVFLTGP |
| Rv3841 | BfrB 181 aa | 8 | MTEYEGPKTK QAVEERNHAM TVTDQVGRLT ANLFELENFV | FHALMQEQIH MLVQHLLDRD AVARDEGDFL AREVDVAPAA | NEFTAAQQYV LRVEIPGVDT GEQFMQWFLQ SGAPHAAGGR | AIAVYFDSED VRNQFDRPRE EQIEEVALMA L | LPQLAKHFYS ALALALDQER TLVRVADRAG |
| Rv1932 | Tpx 165 aa | 9 | MAQITLRGNA IFPSVDTPVC VMPASAFRDS AQEPNYEAAL | INTVGELPAV ATSVRTFDER FGEDYGVTIA AALGA | GSPAPAFTLT AAASGATVLC DGPMAGLLAR | GGDLGVISSD VSKDLPFAQK AIVVIGADGN | QFRGKSVLLN RFCGAEGTEN VAYTELVPEI |
| Rv1352 | None[d] 123 aa | 10 | MARTLALRAS GTYRTEGPSN SVVIPPTVAA | AGLVAGMAMA PLILVFGRVS FQTHNCKLWM | AITLAPGARA ELSTCSWSTH RIS | ETGEQFPGDG SAPEVSNENI | VFLVGTDIAP VDTNTSMGPM |
| Rv3418c | GroES 100 aa | 11 | VAKVNIKPLE WDEDGEKRIP | DKILVQANEA LDVAEGDTVI | ETTTASGLVI YSKYGGTEIK | PDTAKEPQE YNGEEYLILS | GTVVAVGPGR ARDVLAVVSK |
| Rv3875 | ESAT6 95 aa | 12 | MTEQQWNFAG YQGVQQKWDA | IEAAASAIQG TATELNNALQ | NVTSIHSLLD NLARTISEAG | EGKQSLTKLA QAMASTEGNV | AAWGGSGSEA TGMFA |

TABLE 1-continued

Immunodominant Secreted Mtb Proteins identified in CFP[a]

| H37Rv Gene Product | Common Names (length - aa) | SEQ ID NO: | Amino Acid Sequences[c] | | | | |
|---|---|---|---|---|---|---|---|
| Rv1810 | None[d] 118 aa | 13 | MQLQRTMGQC AGITYADPGH AAIASGAYCP | RPMRMLVALL AITAAKAMCG EHLEHHPS | LSAATMIGLA LCANGVTGLQ | APGKADPTGD LVADLRDYNP | DAAFLAALDQ GLTMDSAAKF |
| Rv1980c | MPT64 228 aa | 14 | *VRIKIFMLVT* NINISLPSYY QSAIPPRGTQ DTDPLPVVFP FNPGELLPEA | *AVVLLCCSGV* PDQKSLENYI AVVLKVYQNA IVQGELSQTI AGPTQVLVPR | *ATA*APKTYCE AQTRDKFLSA GGTHPTTTYK GQQVSIAPNA SAIDSMLA | ELKGTDTGQA ATSSTPREAP AFOWQQAYRK GLDPVNYQNF | CQIQMSDPAY YELNITSATY PITYDTLWQA AVTNDGVIFF |
| Rv0350 | DnaK 625 aa | 15 | MARAVGIDLG GQPAKNQAVT RDAEAYLGED AALAYGLDKG GDDWDQRVVD TSINLPYITV GISVSEIDHV LQAGVLKGEV TTADDNQPSV DIDANGIVHV RKRREEADVR AKAALGGSDI PGGAHPGSAD | TTNSVVSVLE NVDRTVRSVK ITDAVITTPA EKEQRILVFD WLVDKFKGTS DAOKNPLFLD VLVGGSTRMP KDVLLLDVTP QIQVYQGERE TAKDKGTGKE NQAETLVYQT SAIKSAMEKL DVVDAEVVDD | GGDPVVVANS RHMGSDWSIE YFNDAQRQAT LGGGTFDVSL GIDLTKOKMA EQLTRAEFQR AVTDLVKELT LSLGIETKGG IAAHNKLLGS NTIRIQEGSG EKFVKEQREA GQESQALGQA GREAK | EGSRTTPSIV IDGKKYTAPE KDAGQIAGLN LEIGEGVVEV MQRLREAAEK ITQDLLDRTR GGKEPNKGVN VMTRLIERNT FELTGIPPAP LSKEDIDRMI EGGSKVPEDT IYEAAQAASQ | AFARNGEVLV ISARILMKLK VLRIVNEPTA RATSGDNHLG AKIELSSSQS KPFQSVIADT PDEVVAVGAA TIPTKRSETF RGIPQIEVTF KDAEAHAEED LNKVDAAVAE ATGAAHPGGE |
| Rv3044 | FecB 359 aa | 16 | MRSTVAVAVA KPDESCARAA DALCALGLQS AAHPDLILGS IAAVDALITG VLSAVGVDRP EAAAERAAVI LRWVDAPIN | AAVIAASSGC AAADPGPPTR RIVAAALPNS QGLTPQLYPQ FAEHATQVGT PSQRFTDKAY LDSDPWRKLS | GSDQPAHKAS PAHNAAGVSP SSSQPSYLGT LAAIAPTVFT KHDATHFQAS IEIGTTAADL ANRDNRVFVV | QSMITPTTQI EMVQVPAEAQ TVHDLPGVGT AAPGADWENN IVQLTANTMR AKSPDFSAAD NDQVWQTGEG | AGAGVLGNDR RIVVLSGDQL RSAPDLRAIA LRGVGAATAR VYGANNFPAS ADIVYLSCAS MVAARGIVDD |

TABLE 2

Immunodominant Cytosolic Mtb Proteins[b]

| H37Rv Gene Product | Common Names (length - aa) | SEQ ID NO: | Amino Acid Sequence[c] | | | | |
|---|---|---|---|---|---|---|---|
| Rv0577 | None[d] | 6 | See Table 1 | | | | |
| Rv1827 | CFP17 | 7 | See Table 1 | | | | |
| Rv1932 | Tpx | 9 | See Table 1 | | | | |
| Rv3418c | GroES | 11 | See Table 1 | | | | |
| Rv0054 | Ssb 164 aa | 17 | VAGDTTITIV EALFLRCNIW VEVDEIGPSL ASGSFGGGDD | GNLTADPELR REAAENVAES RYATAKVNKA EPPF | FTPSGAAVAN LTRGARVIVS SRSGGFGSGS | FTVASTPRIY GRLKQRSFET RPAPAQTSSA | DRQTGEWKDG REGEKRTVIE SGDDPWGSAP |
| Rv0652 | RpIL 130 aa | 18 | MAKLSTDELL GAAVEAAEEQ PKPLLEKVAK | DAFKEMTLLE SEFDVILEAA EAADEAKAKL | LSDFVKKFEE GDKKIGVIKV EAAGATVTVK | TFEVTAAAPV VREIVSGLGL | AVAAAGAAPA KEAKDLVDGA |
| Rv3029c | FixA 266 aa | 19 | MTNIVVLIKQ REKEAADGIE VIQTGWALAR LRKVSIEGGK AAKKKEVTVL EGGNQIVQYL | VPDTWSERKL GSVTVLTAGP ALGTIEGTEL ITGERETDEG TLAEIGVESD VAQKII | TDGDFTLDRE ERATEAIRKA VIAGNESTDG VFTLEATLPA EVGLANAGST | AADVLDEIN LSMGADKAVH VGGAVPAIIA VISVNEKINE VLASTPKPAK | ERAVEEALQI LKDDGMHGSD EYLGLPQLTH PRFPSFKGIM TAGEKVTDEG |
| Rv3028c | FixB 318 aa | 20 | MAEVLVLVEH KAAGAAKIYV IAGRLAARIG RAGAVEAEPA VVAGGRGVGS | AEGALKKVSA AESOLVOKYL SGLLVDVVDV AGAGEQVSVE AENFSVVEAL | ELITAARALG ITPAVDVLAG REGGVGVHSI VPAAAENAAR ADSLGAAVGA | EPAAVVVGVP LAESSAPAGV FGGAFTVEAQ ITAREPAVAG SRAAVDSGYY | GTAAPLVDGL LIAATADGKE ANGDTPVITV DRPELTEATI PGQFQVGQTG |

TABLE 2-continued

Immunodominant Cytosolic Mtb Proteins[b]

| H37Rv Gene Product (length - aa) | Common Names | SEQ ID NO: | Amino Acid Sequence[c] |
|---|---|---|---|
| | | | KTVSPQLYIA LGISGAIQHR AGMQTSKTIV AVNKDEEAPI FEIADYGVVG DLFKVAPQLT EAIKARKG |
| Rv2428 | AhpC2 195 aa | 21 | MPLLTIGDQF PAYQLTALIG GDLSKVDAKQ PGDYFTTITS DEHPGKWRVV FFWPKDFTFV CPTEIAAFSK LNDEFEDRDA QILGVSIDSE FAHFQWRAQH NDLKTLPFPM LSDIKRELSQ AAGVLNADGV ADRVTFIVDP NNEIQFVSAT AGSVGRNVDE VLRVLDALQS DELCACNWRK GDPTLDAGEL LKASA |
| Rv0440 | GroEL2 540 aa | 22 | MAKTIAYDEE ARRGLERGLN ALADAVKVTL GPKGRNVVLE KKWGAPTITN DGVSIAKEIE LEDPYEKIGA ELVKEVAKKT DDVAGDGTTT ATVLAQALVR EGLRNVAAGA NPLGLKRGIE KAVEKVTETL LKGAKEVETK EQIAATAAIS AGDQSIGDLI AEAMDKVGNE GVITVEESNT FGLQLELTEG MRFDKGYISG YFVTDPERQE AVLEDPYILL VSSKVSTVKD LLPLLEKVIG AGKPLLIIAE DVEGEALSTL VVNKIRGTFK SVAVKAPGFG DRRKAMLQDM AILTGGQVIS EEVGLTLENA DLSLLGKARK VVVTKDETTI VEGAGDTDAI AGRVAQIRQE IENSDSDYDR EKLQERLAKL AGGVAVIKAG AATEVELKER KHRIEDAVRN AKAAVEEGIV AGGGVTLLQA APTLDELKLE GDEATGANIV KVALEAPLKQ IAFNSGLEPG VVAEKVRNLP AGHGLNAQTG VYEDLLAAGV ADPVKVTRSA LQNAASIAGL FLTTEAVVAD KPEKEKASVP GGGDMGGMDF |
| Rv2031c | HspX Acr 144 aa | 23 | MATTLPVQRH PRSLFPEFSE LFAAFPSFAG LRPTFDTRLM RLEDEMKEGR YEVRAELPGV DPDKDVDIMV RDGQLTIKAE RTEQKDFDGR SEFAYGSFVR TVSLPVGADE DDIKATYDKG ILTVSVAVSE GKPTEKHIQI RSTN |
| Rv2626c | None[d] 143 aa | 24 | MTTARDIMNA GVTCVGEHET LTAAAQYMRE HDIGALPICG DDDRLHGMLT DRDIVIKGLA AGLDPNTATA GELARDSIYY VDANASIQEM LNVMEEHQVR RVPVISEHRL VGIVTEADIA RHLPEHAIVQ FVKAICSPMA LAS |
| Rv1211 | None[d] 75 aa | 25 | MLGADQARAG GPARIWREHS MAAMKPRTGD GPLEATKEGR GIVMRVPLEG GGRLVVELTP DEAAALGDEL KGVTS |
| Rv1240 | Mdh 329 aa | 26 | VSASPLKVAV TGAAGQIGYS LLFRLASGSL LGPDRPIELR LLEIEPALQA LEGV+VMELDD CAFPLLSGVE IGSDPQKIFD GVSLALLVGA RPRGAGMERS DLLEANGAIF TAQGKALNAV AADDVRVGVT GNPANTNALI AMTNAPDIPR ERFSALTRLD HNRAISQLAA KTGAAVTDIK KMTIWGNHSA TQYPDLFHAE VAGKNAAEVV NOQAWIEDEF IPTVAKRGAA ITDARGASSA ASAASATIDA ARDWLLGTPA DDWVSMAVVS DGSYGVPEGL ISSFPVTTKG GNWTIVSGLE IDEFSRGRID KSTAELADER SAVTELGLI |
| Rv1626 | None[d] 205 aa | 27 | MTGPTTDADA AVPRRVLIAE DEALIRMDLA EMLREEGYEI VGEAGDGQEA VELAELHKPD LVIMDVKMPR RDGIDAASEI ASKRIAPIVV LTAFSQRDLV ERARDAGAMA YLVKPFSISD LIPAIELAVS RFREITALEG EVATLSERLE TRKLVERAKG LLQTKHGMTE PDAFKWIQRA AMDRRTTMKR VAEVVLETLG TPKDT |
| Rv0733 | Adk 181 aa | 28 | VRVLLLGPPG AGKGTQAVKL AEKLGIPQIS TGELFRRNIE EGTKLGVEAK RYLDAGDLVP SDLTNELVDD RLNNPDAANG FILDGYPRSV EQAKALHEML ERRGTDIDAV LEFRVSEEVL LERLKGRGRA DDTDDVILNR MKVYRDETAP LLEYYRDQLK TVDAVGTMDE VFARALRALG K |
| Rv2461c | ClpP 200 aa | 29 | VSQVTDMRSN SQGLSLTDSV YERLLSERII FLGSEVNDEI ANRLCAQILL LAAEDASKDI SLYINSPGGS ISAGMAIYDT MVLAPCDIAT YAMGMAASMG EFLLAAGTKG KRYALPHARI LMHQPLGGVT GSAADIAIQA EQFAVIKKEM FRLNAEFTGQ PIERIEADSD RDRWFTAAEA LEYGFVDHII TRAHVNGEAQ |
| Rv0952 | SucD 303 aa | 30 | MTHMSIFLSR DNKVIVQGIT GSEATVHTAR MLRAGTQIVG GVNARKAGTT VTHEDKGGRL IKLPVFGSVA EAMEKTGADV SIIFVPPTFA KDAIIEAIDA EIPLLVVITE GIPVQDTAYA WAYNLEAGHK TRIIGPNCPG IISPGQSLAG |

TABLE 2-continued

Immunodominant Cytosolic Mtb Proteins[b]

| H37Rv Gene Product (length - aa) | Common Names | SEQ ID NO: | Amino Acid Sequence[c] |
|---|---|---|---|
| | | | ITPANITGPG PIGLVSKSGT LTYQMMFELR DLGFSTAIGI GGDPVIGTTH IDAIEAFERD PDTKLIVMIG EIGGDAEERA ADFIKTNVSK PVVGYVAGFT APEGKTMGHA GAIVSGSSGT AAAKQEALEA AGVKVGKTPS ATAALAREIL LSL |

Footnotes to Tables 1 and 2:
[a]identified by 2-D liquid phase electrophoresis the Mtb culture filtrate protein fractions
[b]identified by 2-D liquid phase electrophoresis of cytosolic fractions. Some cytosolic proteins are also secreted, hence the presence of four proteins from Table 1 in Table 2.
[c]These sequences, obtained from GenBank which includes the fully sequenced Mtb genome. The sequence shown in this table is the complete protein sequence encoded by the open reading frame. Secreted proteins are synthesized with an N terminal secreted signal sequence ("SEC-dependent signal secretion sequence") which may include up to as many as 35 or 40 of the N-terminal residues. Signal sequences of several of the proteins are indicated in the table by underscore and italics. This sequenceis cleaved from the secreted protein. When used as immunogens, the secreted proteins lack this secreted signal sequence. Sequences were obtained using MS or MS/MS data of peptides generated by trypsin digestion and were identified using the MSFit (25) or Sequest (26) programs, respectively.
[d]The present inventors and their colleagues were the first to identify a protein with a specific function or biological activity (stimulation of T cells in infected mice) for this previously recognized open reading frame of the Mtb genome.

A functional derivative thus includes a "homologue," "fragment," "variant," "analogue," or "chemical derivative" of the antigenic Mtb protein of this invention. "Functional derivatives" encompass "variants" and "fragments" regardless of whether the terms are used in the conjunctive or the alternative herein.

A functional derivative retains at least a portion of the function of the full length protein which permits its utility in accordance with the present invention, namely, the ability to induce heightened resistance to Mtb challenge when administered in mid-life to a BCG vaccinated subject A "fragment" of the antigenic Mtb protein refers to any subset of the molecule, that is, a shorter peptide. An "analogue" of the antigenic Mtb protein refers to a non-natural molecule substantially similar to either the entire molecule or a fragment thereof.

Preferred fragments of the full length Mtb protein are booster vaccine epitopes which stimulate $T_H1$ cells from subjects primed by earlier BCG vaccination.

A "variant" refers to a polypeptide or peptide molecule substantially similar to either the entire protein or the fragment thereof. Variant peptides may be conveniently prepared by direct chemical synthesis using methods well-known in the art. A preferred group of variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

Another useful functional derivative is a fusion protein, a polypeptide that includes a functional fragment of the immunogenic Mtb protein. The presence of the fusion partner can alter the solubility, affinity and/or valency (defined here as the number of binding sites available per molecule) of the Mtb protein.

Homologues

A functional homologue must possess the above biological activity. In view of this functional characterization, use of homologous proteins from other mycobacterial species, including proteins not yet discovered, fall within the scope of the invention if these proteins have sequence similarity and the recited biochemical and biological activity.

To determine the percent identity of two amino acid sequences (or of two nucleic acid sequences), the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence.

For example, when aligning a second sequence to a particular immunogenic Mtb protein, e.g., Ag85A (SEQ ID NO:1) having 295 amino acid residues, at least 90, preferably at least 118, more preferably at least 148, even more preferably at least 177, and even more preferably at least 207, 236 or 266 amino acid residues are aligned. The amino acid residues (or nucleotides) at corresponding amino acid positions (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to Mtb Ag85A-encoding nucleic acid molecules. BLAST protein searches can be performed with the XBLAST program, score=50, wordlength=3 to obtain amino acid sequences homologous to Mtb Ag85A protein molecules of the invention. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

In another embodiment, a homologue is defined as having a sequence similarity the statistical significance of which results in a z value exceeding 10 when the sequence of the homologue is compared to the sequence of the native protein using a program such as BLAST (XBALST) above, or an earlier program such as FASTA or FASTP, coupled with a Monte Carlo analysis as described by W. R. Pearson and D. J. Lipman, *Proc Natl Acad Sci USA.,* 85:2444-2448, 1988.

Thus, for example, a homologue of the Mtb Ag85A protein described above is characterized as having (a) functional activity of native Mtb Ag85A and (b) sequence similarity to a native Mtb Ag85A protein (SEQ ID NO:31) of at least about 30% (at the amino acid level), preferably at least about 50%, more preferably at least about 70%, even more preferably at least about 90%.

It is within the skill in the art to obtain and express such a protein using DNA probes based on the disclosed sequences of Mtb Ag85A. Then, the protein's biochemical and biological activity can be tested readily using art-recognized methods such as those described herein, for example, a standard T cell proliferation or IFNγ secretion assay. Preferred assays measure the functional characteristics of Mtb Ag85A such as stimulating T cells synthesis of cytokines, particularly IFNγ. The binding of Mtb Ag85A epitopes processed by antigen presenting cells to its cognate T cell receptor on, for example, $T_H1$ cells, transmits a signal that induces increased cytokine production; if the cytokine is a growth factor such as IL-2, it stimulates proliferation which can also be measured routinely.

All the native DNA sequences encoding the native proteins that are within the scope of this invention are publicly available on GenBank (or other public databases). A number of processes can be used to generate fragments, mutants and variants of the isolated DNA sequence. Small subregions or fragments of the nucleic acid encoding the immunogenic Mtb protein, for example 1-30 bases in length, can be prepared by standard, chemical synthesis.

Chemical Derivatives

A "chemical derivative" of the Mtb protein contains additional chemical moieties not normally a part of the peptide. Covalent modifications of the polypeptide or peptide are included within the scope of this invention. Such modifications may be introduced into the molecule by reacting targeted amino acid residues of the peptide with an organic derivatizing agent that is capable of reacting with selected side chains or terminal residues.

Covalent modifications of the polypeptide or peptide are included and may be introduced by reacting targeted amino acid residues of the peptide with an organic derivatizing agent that is capable of reacting with selected side chains or terminal residues.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N- alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5-7.0) which agent is relatively specific for the histidyl side chain. p-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing α-amino-containing residues include imidoesters such as methylpicolinimidate;

pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high $pK_a$ of the guanidine functional group. Furthermore, these reagents may react with the groups of lysine as well as the arginine ε-amino group.

Modification of tyrosyl residues has permits introduction of spectral labels into a peptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the peptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane.

Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other chemical modifications include hydroxylation of proline and lysine, phosphorylation of the hydroxyl groups of seryl or threonyl residues, methylation of the α-amino groups of lysine, arginine, and histidine side chains (T. E. Creighton, supra), acetylation of the N-terminal amine, and, in some instances, amidation of the C-terminal carboxyl.

Such chemically modified and derivatized moieties may improve the protein's or peptide's solubility, absorption, biological half life, and the like. These changes may eliminate or attenuate undesirable side effects of the proteins in vivo. Moieties capable of mediating such effects are disclosed, for example, in *Remington's Pharmaceutical Sciences*, Mack Publishing Company, Easton Pa. (Gennaro 18th ed. 1990).

Vaccine Compositions and their Formulation

This invention includes a vaccine composition for boosting anti-Mtb protective immunity during midlife in a BCG-vaccinated subject. An Mtb immunogenic protein preferably one of the proteins described herein in more detail, is formulated as the active ingredient in a vaccine composition.

The vaccine compositions preferably comprises any of the following proteins (in their secreted form if they are secreted proteins), or preferably, a mixture of two or more of: Rv3804c, Rv1886c, Rv0129c, Rv1860, Rv0934, Rv0577, Rv1827, Rv3841, Rv1932, Rv1352, Rv3418c, Rv3875, Rv1810, Rv1980c, Rv0350, Rv3044, Rv0054, Rv0652, Rv3029c, Rv3028c, Rv2428, Rv0440, Rv2031c, Rv2626c, Rv1211, Rv1240, Rv1626, Rv0733, Rv2461c, and Rv0952. A most preferred vaccine composition includes Rv3804c or one or more epitopes thereof as a single or one of a mixture of immunogenic molecules.

The vaccine may also comprises one or more peptides or other functional derivatives of these proteins as described, or DNA encoding the protein (in the form of a DNA vaccine), and a pharmaceutically and immunologically acceptable vehicle or carrier. In one embodiment, the vaccine comprises a fusion protein which includes at least one immunogenic epitope of the Mtb protein.

As described in more detail, the vaccine composition preferably also comprises an adjuvant or other immune stimulating agent. For use in vaccines, the Mtb antigenic protein or epitope-bearing peptide thereof is preferably produced recombinantly, preferably in prokaryotic cells as noted above.

Full length proteins or longer multiple epitope-bearing fragments are preferred immunogens, in particular, those reactive with T cells, particularly those that stimulate IFNγ production by T cells. If a shorter epitope-bearing fragment, for example containing 20 amino acids or less, is the active ingredient of the vaccine, it is advantageous to couple the peptide to an immunogenic carrier to enhance its immunogenicity or to fuse a number of repeating units of the epitope in a single polypeptide chain. Such coupling techniques are well known in the art, and include standard chemical coupling techniques using linker moieties such as those available from Pierce Chemical Company, Rockford, Ill. Suitable carriers are described below.

Another embodiment is a fusion protein which comprise the Mtb protein or epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions that are not part of the same protein in its native form can be "mixed and matched" in a single fusion polypeptide.

The active ingredient, preferably a recombinant product, is preferably administered as a protein or peptide vaccine. However, as noted, the vaccine composition may also comprise a DNA vaccine (e.g., Hoffman, S L et al., 1995, *Ann N Y Acad Sci* 772:88-94; Donnelly, J J et al., 1997, *Annu Rev Immunol* 15:617-48; Robinson, H L, 1997, *Vaccine.* 15: 785-787, 1997; Wang, R et al., 1998, Science. 282: 476-480, 1998; Gurunathan, S et al., 2000, Annu Rev Immunol 18:927-74; Restifo, N P et al., 2000, *Gene Ther.* 7:89-92). The DNA encodes the Mtb protein or one or more epitope(s) thereof, and may be optionally linked to DNA encoding a protein that promotes expression of the Mtb protein in the host after immunization. Known examples of such proteins include heat shock protein 70 (HSP70) (Srivastava, P K et al., 1994. *Immunogenetics* 39:93-8; Suto, R et al., 1995, *Science* 269:1585-8; Arnold-Schild, D et al., 1999, *J Immunol* 162:3757-60; Binder, R J et al., 2000, *Nature Immunology* 2:151-155; Chen, C H et al., 2000, *Cancer Res* 60:1035-42) or translocation proteins such herpesvirus protein VP22 (Elliott, G, and O'Hare, P., 1997. *Cell* 88:223-33; Phelan, A et al., 1998, *Nat Biotechnol* 16:440-3; Dilber, M S et al., 1999. *Gene Ther* 6:12-21) or domain 11 of *Pseudomonas aeruginosa* exotoxin A (ETA) (Jinno, Y et al., J Biol. Chem. 264: 15953-15959, 1989; Siegall, C B et al., Biochemistry. 30: 7154-7159, 1991; Prior, T I et al., Biochemistry. 31: 3555-3559, 1992; Fominaya, J et al., J. Biol. Chem. 271: 10560-10568, 1996; Fominaya, J et al., Gene Ther. 5: 521-530, 1998; Goletz, T J et al., Hum Immunol. 54: 129-136, 1997).

In another embodiment, the vaccine is in the form of a strain of bacteria (preferably a known "vaccine strain") which has been genetically transformed to express the Mtb protein or epitope-bearing peptide. Some known vaccine strains of *Samonella* are a live vaccine strain of *Salmonella dublin*, termed SL5928 aroA148fliC(i)::Tn10 and *S. typhimurium* LB5000 hsdSB121 leu-3121 (Newton S. M. et al., Science 1989, 244: 70

A *Samonella* strain expressing the Mtb protein or fragment of this invention may be constructed using known methods. Thus, a plasmid encoding the protein or peptide. The plasmid may first be selected in an appropriate host, e.g., *E. coli* strain MC1061. The purified plasmid is then introduced into *S. typhimurium* strain LB5000 so that the plasmid DNA is be properly modified for introduction into *Samonella* vaccine strains. Plasmid DNA isolated from LB5000 is introduced into, e.g., *S. dublin* strain SL5928 by electroporation. Expression of the Mtb protein or fragment encoded by the plasmid in SL5928 can be verified by Western blots of bacterial lysates and antibodies specific for the relevant antigen or epitope.

Formulation of the Polypeptide Vaccine

The protein/peptide composition that is formulated as a vaccine can be the whole target protein or fragments thereof. The immunogenicity of the present Mtb protein/peptide immunogen a is enhanced in the presence of exogenous adjuvants, immune stimulants, depot materials, etc.

In some cases, the immunogenicity or effectiveness of the Mtb protein/peptide may benefit from its being conjugated to a suitable carrier, usually another larger protein molecule that is foreign to the host being immunized. In such a construct, multiple copies of the polypeptide may be conjugated to a single larger carrier molecule. The carrier may have properties which facilitate transport, binding, absorption or transfer of the polypeptide immunogen. Conjugation between proteinaceous materials is readily accomplished using conventional methods, e.g., bifunctional cross-linkers as binding agents (Means et al., *Bioconjugate Chem.* 1:2-12 (1990)). Examples of suitable carriers are the tetanus toxoid, the diphtheria toxoid, serum albumin, keyhole limpet hemocyanin proteins *E. coli* pilin protein 99, BSA, rotavirus VP6 protein, and the like. Conjugates including these "universal" carriers can stimulate T cell responses (preferably T helper cells) in a less MHC-restricted manner than would occur without them.

The immunogenic Mtb protein/peptide may be combined or mixed with various fluids and with other substances known in the art. The polypeptide is formulated conventionally using methods well-known for formulation of such vaccines. The active ingredient is generally dissolved or suspended in an acceptable carrier such as water, saline or buffered saline.

The vaccine composition may further comprise one or more adjuvants or immunostimulating agents. Examples of adjuvants or agents that may add to the effectiveness of the protein as an immunogen include aluminum hydroxide, aluminum phosphate, aluminum potassium sulfate (alum) beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium* acnes or *Bordetella pertussis*, polyribonucleotides, sodium alginate, lanolin, lysolecithin, vitamin A, saponin and saponin derivatives (such as QS-21 a purified triterpene glycoside from the South American tree *Quillaja saponarial*(Soltysik, S et al., *Ann N Y Acad Sci*. (1993) 690:392-395, liposomes, levamisole, DEAE-dextran, blocked copolymers or other synthetic adjuvants. Another adjuvant is ISAF-1 (5% squalene, 2.5% pluronic L121, 0.2% Tween 80 in phosphate-buffered solution with 0.4 mg of threonyl-muramyl dipeptide (Kwak, L W et al., (1992) *N. Engl. J. Med.,* 327: 1209-1238). Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Aluminum is approved for human use. The vaccine material may be adsorbed to or conjugated to beads such as latex or gold beads, ISCOMs, and the like. General methods to prepare vaccines are described in Remington's Pharmaceutical Science; Mack Publishing Company Easton, Pa. (latest edition).

A most preferred adjuvant for the Mtb proteins, such as exemplified for Antigen 85A, is monophosphoryl lipid A adjuvant solubilized in 0.02% triethanolamine plus an effective amount of recombinant IL-2 cytokine.

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., *Immunological Adjuvants and Vaccines*, Plenum Press, New York, 1989 Michalek, S. M. et al., *Curr. Top. Microbiol. Immunol.* 146:51-58 (1989).

Additional discussion of vaccine design, particularly controlled release systems, can be found in Powell, M. F. et al. (eds), *Vaccine Design: The Subunit and Adjuvant Approach*, Powell, M. F. et al. (eds), Plenum Press, New York 1995, p 389-412. Controlled release systems are already used in humans as "depots" to deliver drugs and hormones (Langer, R. 1990, *Science* 249: 1527-1533). Such systems may have a significant impact on immunization as they can be designed to deliver controlled amounts of antigen continuously or in spaced pulses at predetermined rates (Cohen et al., 1991, *Pharm. Res.* 8:713-720; Eldridge et al., 1991a, *Mol. Immunol.* 28:287-294; Gander et al. 1993, in: *Proc. Int. Syn. Control. Rel. Bioact. Mater.*, Controlled Release Society, Washington, D.C., pp. 65-66), while simultaneously protecting undelivered antigen from rapid degradation in vivo. Controlled release microspheres have considerable potential for oral immunization (Edelman et al., 1993, *Vaccine* 11:155-158; Eldridge et al., 1990, *J. Control. Rel.* 11:205-214; McQueen et al., 1993, *Vaccine* 11:201-206; Moldoveanu et al., 1989, *Curr Top. Microbiol. Immunol.* 146:91-99; O'Hagan et al., 1993b, *Vaccine* 11: 149-154; Reid et al. 1993, *Vaccine* 11:159-167). Other potential advantages of polymeric controlled release systems include: lower dosage requirements leading to decreased cost; localized or targeted delivery of antigen to antigen-presenting cells or the lymphatic system; more than one antigen may be encapsulated, facilitating the design of a formulation that can immunize an individual against more than one protein or against several epitopes of an Mtb protein in a single injection; and improved patient compliance. In addition, a controlled release systems may reduce the number of vaccine doses required for optimal vaccination to a single injection.

Microspheres are particularly suited as controlled release vaccine carriers for two reason: (1) particles greater than 10 μm in diameter are capable of providing a long-term persistence of antigen at the site of injection which may be necessary for a sustained high-level antibody immune response and (2) microparticles in the size range of 1-10 μm are readily phagocytosed by macrophages (Eldridge et al., 1989, *Adv. Exp. Med. Biol.* 251:192202; Tabata et al., 1988, *Biomaterials* 9:356-362; *J. Biomed Mater Res.* 22:837-858) leading to direct intracellular delivery of antigen to antigen-presenting cells.

Microsphere phagocytosis by macrophages may be increased by altering the surface characteristics, as microspheres with hydrophobic surfaces are generally more readily phagocytosed than those with hydrophilic surfaces (Tabata et al., 1988, *Biomaterials* 9:356-362; Tabata et al., 1990, *Crit. Rev. Ther Drug Carrier Syst.* 7:121-148).

Among the advantages of using polymer microspheres for vaccine delivery is the ability to control the time following administration at which the antigen is released. This capability allows the fabrication of a single-injection formulation that releases multiple "pulses" of vaccine at predetermined times following administration (Gilley et al., 1992, In: *Proc. Int. Symp. Control. Rel. Bioact. Mater*, Controlled Release Society, Orlando, pp. 110-111). Antigen release kinetics from polymer microspheres can be controlled to a great extent by the simple manipulation of such variable as polymer composition and molecular weight, the weight ratio of vaccine to polymer (i.e., the vaccine loading), and microsphere size (Hanes et al., In: *Reproductive Immunology,* 1995, R. Bronson et al., eds, Blackwell. Oxford).

Vaccine formulations that contain a combination of both small (1-10 μm) and larger (20-50 μm) microspheres may produce higher and longer-lasting responses compared to the administration of vaccine encapsulated in microspheres with diameters of exclusively 1-10 or 20-50 μm (Eldridge et al., 1991a, *Mol. Immunol.* 28287-294). In one study, tetanus toxoid (TT)-containing microspheres were tailored to produce a strong priming antigen dose released over the first few days after injection followed by two "boosting" doses released after 1 and 3 months, respectively, in order to mimic conventional vaccination schedules (Gander et al., supra).

The most widely used polymers for vaccine microencapsulation have been the polyesters based on lactic and glycolic acid. These polymers have several advantages, including extensive data on their in vitro and in vivo degradation rates (Lewis, 1990, In: *Biodegradable Polymers as Drug Delivery Systems* (Chasin and Langer, eds.), Dekker, New York, pp. 1-41; Tice and Tabibi, 1992, In: *Treatise on Controlled Drug Delivery* (A. Kydonieus, ed.), Dekker, New York, pp. 315-339, and FDA approval for a number of clinical applications in humans such as surgical sutures (Gilding et al., 1979, *Polymer* 20:1459-1464; Schneider, 1972, U.S. Pat. No. 3,636,956) and a 30-day microsphere-based controlled delivery system for leuprolide acetate (Lupron Depot) (Okada et al., 1991, *Pharm. Res.* 8:787-791).

There are several interesting alternatives to the lactide/glycolide polyesters. For example, some biodegradable polymers degrade to give molecules with adjuvant properties, and may prove particularly useful as carriers of more weakly immunogenic antigens. Because of the know adjuvanticity of L-tyrosine derivatives (Wheeler et al, 1982, *Int. Arch. Allergy Appl. Immunol.* 69:113-119; Wheeler et al., 1984, *Int. Arch. Allergy Appl. Immunol.* 75:294-299), a polymer based on a dityrosine derivative was synthesized by Langer and colleagues (Kohn et al., 1987, *Biomaterials* 7:176-182) and was studied using the model antigen bovine serum albumin, BSA (Kohn et al., 1986, *J. Immunol. Methods* 95:31-38). Biodegradable poly (CTTH iminocarbonate) was selected since its primary degradation product N-benzyloxycarbonyl-L-tyrosyl-L-tyrosine hexyl ester (CTTH), was found to be as potent an adjuvant as complete Freund's (CFA) and muramyl dipeptide (MDP).

Because of its inherent propensity to be phagocytosed by macrophages (Tabata et al., 1986, *J. Bioact. Compat. Polym.* 1:32-46) and its extensive use in pharmaceutical and medical applications, gelatin is a useful polymer for vaccine microencapsulation (Tabata et al., 1993, in: *Proc. Int. Symp. Control. Rel. Bioact. Mater*, Controlled Release Society, Washington, D.C., pp. 392-393). Gelatin microspheres have also been used to encapsulate immunostimulators, such as MDP and interferon-α (Tabata et al., 1987, *J. Pharm. Pharmacol.* 39:698-704; 1989b, *Pharm. Res.* 6:422-427). Microsphere-encapsulated MDP activated macrophages in much shorter periods than did free MDP at concentrations approximately 2000 times lower. A combination of MDP and vaccine-containing gelatin microspheres may yield a very potent vaccine formulation.

Liposomes are often unstable in vivo, most likely because of their rapid destruction by macrophages and high-density lipoproteins (Schreier et al., 1987, *J. Control. Rel.* 5: 187-192), and therefore provide only a brief antigen depot effect when injected subcutaneously or intramuscularly (Eppstein et al., 1985, *Proc. Natl. Acad. Sci. USA* 82:3688-3692; Weiner et al., 1985, *J. Pharm. Sci.* 74:922-925). One approach to extending the in vivo lifetime of liposomes (Cohen et al., 1991, *Proc. Natl. Acad. Sci. USA* 88:10440-10444) was use of alginate polymers to encapsulate vaccine-containing liposomes into microspheres, thereby protecting them from rapid destruction in vivo. Enzymatically activated microencapsulated liposomes (MELs) that are capable of providing pulsatile vaccine release kinetics have also been prepared (Kibat et al., 1990, *FASEB J.* 4:2533-2539). MELs are also expected to show increased stability as a carrier for oral administration.

Microsphere Production

A variety of methods may be used to prepare vaccine-loaded polymer microspheres that are capable of a wide range of release patterns and durations. The method of choice usually is determined by the relative compatibility of the process conditions with the antigen (e.g., the method that results in the least loss of vaccine immunogenicity) and the polymer excipient used, combined with the ability of the method to produce appropriately sized microspheres.

Solvent evaporation techniques are popular because of their relative ease of preparation, amenability to scaleup, and because high encapsulation efficiencies can be attained. Of particular importance for vaccines that are sensitive to organic solvents may be the multiple emulsion technique (Cohen et al., 1991, *Pharm. Res*., supra). Spray drying and film casing techniques have also been used to prepare monolithic polymer microspheres.

Microcapsules consist of a vaccine-loaded core surrounded by a thin polymer membrane and, as a result, are often referred to as "reservoir" systems.

Carrier and vaccine stability during device development, storage, and in vivo depoting are a matte for concern. Polypeptide antigens may have with fragile three-dimensional structures that are vital to the immunogenicity of the vaccine. This three-dimensional structure may be compromised or lost as the antigen denatures or aggregates. Exposure to organic solvents, rehydration after lyophilization on exposure to moisture, or complex chemical interactions with the polymer excipient or other chemicals in the preparation of a controlled release device may result in loss or reduction of immunogenicity of protein-based vaccines. The following documents describe stabilization of complex antigens (Arakawa et al., 1993, *Adv. Drug Deliv. Rev.* 10:1-28; Liu et al., 1991, *Biotechnol. Bioeng.* 37:177-184; Volin and Klibanov, 1989, In: *Protein Function: A Practical Approach* (T. E. Creighton, ed.). IRL Press, Oxford, pp. 1-24).

An advantage of polymer microsphere formulations is that many polymers are stable at room temperature for extended periods of time if kept dry. For example, lactide/glycolide polyesters have been reported to be stable if kept dry and below about 40° C. (Aguado et al., 1992, *Immunobiology* 184:113-125). In addition, vaccine can be stored in the dry state within microsphere formulations, an important advantage considering susceptibility of some proteins to moisture-induced aggregation (Liu et al., supra).

The vaccine compositions preferably contain (1) an effective amount of the immunogenic Mtb polypeptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

In one embodiment, the vaccine composition includes one or more cytokines such as IL-2, GM-CSF, IL-4 and the like. Proinflammatory chemokines may be added, e.g., interferon inducible protein 10 and MCP-3 (Biragyn A et al., *Nature Biotechnol*. (1999) 17:253-258). In general, it appears that any cytokine or chemokine that induces inflammatory responses, recruits antigen presenting cells (APC) and promotes targeting of APC for chemokine receptor-mediated uptake of the polypeptide antigen leading to the generation of critical T cells, is useful in the present vaccine formulation.

As with all immunogenic compositions for eliciting cell-mediated immunity, the immunogenically effective amounts of the polypeptides of the invention must be determined empirically. Factors to be considered include the immunogenicity of the native polypeptide, whether or not the polypeptide will be complexed with or covalently attached to an adjuvant or carrier protein or other carrier and the route of administration and the number of immunizing doses to be administered. Such factors are known in the vaccine art, and it is well within the skill of immunologists to make such determinations without undue experimentation.

The proportion of the protein immunogen and the adjuvant can be varied over a broad range so long as both are present in effective amounts. For example, aluminum hydroxide can be present in an amount of about 0.5% of the vaccine mixture ($Al_2O_3$ basis).

After formulation, the vaccine composition may be incorporated into a sterile container which is sealed and stored at a low temperatures, for example 4° C. or −20° C. or −80° C. Alternatively, the material may be lyophilized which permits longer-term storage in a stabilized form.

Administration and Dosage

The vaccines are administered as is generally understood in the art. Ordinarily, systemic administration is by injection; however, other effective means of administration are known. With suitable formulation, polypeptide vaccines may be administered across the mucus membrane using penetrants such as bile salts or fusidic acids in combination, usually, with a surfactant. Transcutaneous administration of polypeptides is also known. Oral formulations can also be used.

Dosage levels depend on the mode of administration, the nature of the subject, and the nature of carrier/adjuvant formulation. Preferably, an effective amount of the protein or polypeptide is between about 0.01 μg/kg and about 1 mg/kg body weight. The amount of the immunogen per dose can range from about 0.01 mg to 100 mg of protein per subject per injection. A preferably range is from about 0.2 to 2 mg per dose. A suitable unit dose size is about 0.5 ml. Accordingly, a unit dosage form for subcutaneous injection could comprise 0.5 mg of immunogen admixed with 0.5% aluminum hydroxide in 0.5 ml.

Administration is preferably by injection on one or multiple occasions to boost the immune system to a state of systemic immunity. In general, multiple administrations of the vaccine in a standard immunization protocol are used, as is standard in the art. For example, the vaccines can be administered at approximately two to six week intervals, preferably monthly, for a period of from one to six inoculations in order to provide protection.

In a preferred embodiment, a BCG-vaccinated human subject receives a single booster injection of the Mtb protein at the age of about 10 years. After this first booster dose of the vaccine, the subject may optionally receive additional injections if this is determined to be efficacious, e.g., once a month for 6 months, but preferably no more than annually. It is within the skill of the art to determine empirically how many doses and what magnitude of dose are deemed optimal.

The vaccine may be administered by any conventional route including oral and parenteral. Examples of parenteral routes are subcutaneous, intradermal, transcutaneous, intravenous, intramuscular, etc.

Vaccination with the vaccine composition will result in a systemic immune response, which includes preferably a cell-mediated immune response and may also include an antibody response. This should provide an antimicrobial therapeutic effect and/or result in a activated T lymphocytes of various classes. In addition such T cells have a number of research uses that are evident to those skilled in the art.

Having now generally described the invention, the same will be more readily understood through reference to the following examples which are provided by way of illustration, and are not intended to be limiting of the present invention, unless specified.

EXAMPLE I

Materials and Methods

Growth of *M. tuberculosis*, and Preparation of Culture Filtrate and Cytosolic Proteins

*M. tuberculosis* $H_{37}$Rv (ATCC 27294) was obtained from the American Type Culture Collection (Rockville, Md.). Initially, this strain was inoculated from a 1-mL frozen stock of approximately $10^8$ CFU/mL into 10 mL of glycerol-alanine-salts medium (Takayama, K et al., *J. Lipid Res.* 1975, 16:308-317). This initial culture was expanded to a total of 30 liters as described by Sonnenberg et al., supra.

After incubation at 37° C. for 14 days with gentle agitation the culture supernatant was separated from the cells by filtration through a 0.2 μm membrane. The cells were collected, washed three times with PBS pH 7.4 and frozen at −70° C. until needed. The culture filtrate was concentrated by ultrafiltration with a 10 kDa molecular cut off membrane, dialyzed against 10 mM ammonium bicarbonate (Dobos, K M et al., *Infect. Immun.* 1996, 63:2846-285319), and the protein concentration determined by the bicinchoninic acid (BCA) protein assay (Smith, P K et al., *Anal. Biochem.* 1985, 150:76-85). Three lots of cells and CFPs were prepared in this fashion and pooled.

The *M. tuberculosis* H37Rv cells (103.2 g) were inactivated with 2.4 megarads of γ-irradiation. These cells were suspended in 50 mL of PBS pH 7.4 containing 0.06% DNase, 0.06% RNase, 0.07% pepstatin, 0.05% leupeptin, and 20 mM PMSF. The cell suspension was and passed through a French Press (American Instrument Co., Silver Spring, Md.) six times at 1,500 psi. The resulting lysate was diluted with 2 vol of the cell suspension buffer and centrifuged at 3,000×g for 5 minutes to remove unbroken cells. The supernatant was collected and subjected to centrifugation at 27,000×g, 4° C. for 1 h to remove cell wall material followed by centrifugation at 100,000×g, 4° C. for 4 h to remove cell membranes. The final supernatant (cytosol fraction) was collected and exhaustively dialyzed against 10 mM ammonium bicarbonate using a 3,500 Da molecular weight cutoff membrane. The final protein concentration of the cytosol was determined with BCA protein assay.

Preparative Liquid-Phase Isoelectric Focusing

CFPs (500 mg) and cytosol proteins (one lot of 100 mg and another of 150 mg) were each solubilized in 60 mL of a buffer containing 8M urea, 1 mM DTT, 5% glycerol, 2% NP-40, and 2% ampholytes (pH 3.0 to 10.0 and pH 4.0 to 6.5 in a ratio of 1:4) ("Pharmalytes," Pharmacia Biotech AB, Uppsala, Sweden) and loaded on a Bio-Rad Rotofor System (Hercules, Calif.). The Rotofor apparatus was cooled to 4° C. Constant power (12 W) was applied until the voltage stabilized at approximately 1400 V. Focusing was continued for an additional 30 minutes and then terminated. The individual IEF fractions were harvested and their pH value determined. Finally, each IEF fraction was dialyzed against 10 mM ammonium bicarbonate using a 3,500 Da molecular cutoff membrane, the protein concentrations were determined using the BCA assay, and an aliquot (10 μg) was subjected to SDS-PAGE (Laemmli, U. K., *Nature* 1970, 227, 680-685) and the proteins visualized by staining with silver-nitrate (Morrissey, J. H., *Anal. Biochem.* 1981, 117, 307-310).

Preparative SDS PAGE and Electroelution

Preparative SDS-PAGE was performed on 0.2 to 10 mg aliquots of individual preparative IEF fractions. Briefly, each preparative IEF fraction was prepared for SDS-PAGE by the addition of 0.2 vol of 5× SDS-PAGE sample buffer (Laemmli, supra) and heating at 100° C. for 10 min. The reduced samples were loaded on 16×20 cm polyacrylamide gels that were comprised of a 6% stack over a 15% resolving gel. The stacking gel contained a single 13 cm sample well. Electrophoresis was performed at 35 mA per gel until the dye front was approximately 2 cm from the bottom of the gel. The gels were subsequently soaked for 15 to 20 min in 10 mM ammonium bicarbonate, cut to the appropriate size (14×16 cm), and transferred to a Bio-Rad Whole Gel Eluter according to manufacturer's instructions. The proteins were eluted from the gel using 250 mA constant current for 1 hour (Andersen et al., 1993, supra). Thirty protein fractions (approximately 2.5 mL each) were harvested, dialyzed against 10 mM ammonium bicarbonate using a 3,500 Da molecular cutoff membrane, and the protein concentration of each fraction was determined using the BCA protein assay. An aliquot (~2 μg) of each preparative SDS-PAGE fraction was run on a 10×7.5 cm SDS-polyacrylamide gel and proteins visualized by staining with silver nitrate. The remaining quantity of each fraction was filter sterilized with a 0.2 um filter (Gelman, Ann Arbor, Mich.), and lyophilized.

In-Gel Digestions and Mass Spectrometry

An aliquot of protein (5-10 μg) was suspended in IEF sample buffer (Sonnenberg et al., supra) and applied to a 6% polyacrylamide IEF tube gel (1.5 mm by 6.5 cm) containing 5% ampholytes (pH 3 to 10 and 4 to 6.5 in a ratio of 4:1). The proteins were focused for 3 h at 1 kV. The tube gels were subsequently soaked in sample transfer buffer (Dunbar, B S et al., *Methods Enzymol.* 1990, 182:441-459) for 20 min and placed on a 15% preparative SDS-polyacrylamide gel (7.5 cm by 10 cm by 1.5 mm). Electrophoresis in the second dimension was carried out at 15 mA per gel for approximately 1.5 h. The gels were stained with Coomassie brilliant blue R-250 in 10% acetic acid and 50% methanol, and destained with 5% methanol 7% acetic acid. The gels were completely rehydrated in water, and the protein spots of interest were excised from the gel, and cut into small pieces. The proteins were destained, digested with modified trypsin (Boehringer Mannheim, Mannheim, Germany) and the peptides extracted with 60% acetonitrile, 0.1% TFA (Hellman, U et al., *Anal. Biochem.* 1995, 224:451-45524). The peptides were dried and suspended in 15 μl of 5% acetonitrile, 0.1% TFA and separated on a 15×0.1 cm C18 microbore reversed-phase column (Vydac, Hesperia, Calif.) connected to a Waters 2690 Separation Module (Milford, Mass.). The peptides were eluted with an increasing acetonitrile gradient at a flow rate of 20 μl per min. The reversed-phase effluent was introduced directly into a Finnigan LCQ (Thermoquest, San Jose, Calif.) electrospray mass spectrometer, and the peptides were analyzed by MS or MS-MS. The ES needle was operated at 6 kV with a sheath gas flow of $N_2$ at 40 and a capillary temperature of 100° C. MS-MS was performed on the fly of the most dominant ion of the previous MS scan and the collision energy was set at 40%. MS and MS-MS data of the peptides was matched to *M. tuberculosis* proteins using MS Fit (Baker, P. R. and Clauser, K. R., http://prospector.ucsf.edu) and the SEQUEST software (Eng, J K et al., *J. Am. Soc. Mass Spectrom.* 1994, 5:976-989; Yates, J R III, et al., *Anal. Chem.* 1995, 67:1426-1436), respectively. Both programs were set to consider oxidation of methionine (+16.0) and polyacrylamide modification of cysteine (+71.0). Mass tolerances of 1.0 Da for intact peptide ions and 0.5 Da for fragment ions were employed.

Infection of Mice with *M. tuberculosis* H37Rv and Harvesting of Splenocytes.

Fourteen C57B1/6 mice were infected by intravenous (iv) challenge with 1×10⁵ cfu of *M. tuberculosis* $H_{37}Rv$ per animal (Orme, I. M., *J. Immunol.* 1987:138, 293-298). Seven infected mice and seven non-infected control mice were euthanized by exposure to $CO_2$ at 10 and 40 days post infection. The spleen of each animal was removed, and spleen cells (primarily lymphocytes) were harvested by flushing the spleens four times with 3 mL of complete RPMI 1640 medium (RPMI medium with 10% fetal calf serum, 50 uM β-mercaptoethanol), followed by passing the spleen remnant through a 70 μm nylon screen. Cells were washed three times with complete RPMI medium and once with Hank's balanced salt solution, followed by lysis of erythrocytes with hypotonic buffer. The enriched lymphocytes were pelleted by centrifugation at 3000×g, washed with complete RPMI medium, and the final pellet of cells suspended in complete RPMI medium at $2.5 \times 10^6$ cells per mL.

Interferon-γ Secretion Assay

Cells harvested from infected and non infected mice were plated at a density of $2 \times 10^5$ cells per well in 96 well plates and individual 2-D LPE fractions (2 μg protein) were added to the cells in triplicate. After four days of incubation at 37° C. and 5% $CO_2$, the supernatants from these cultures were assayed for the presence of IFNγ by plate ELISA using the IFNγ kit from Genzyme Diagnostics (Cambridge, Mass.). Quantitation of IFNγ was performed by reading the ELISA plates at A405 and plotting the data against a standard curve of IFNγ. The standard error was within 10% of the mean values.

EXAMPLE II

2-D Liquid Phase Electrophoresis of Culture Filtrate and Cytosolic Proteins

To ensure sufficient protein quantities for both immunological analysis and molecular identification, large aliquots of CFPs (500 mg) and cytosolic proteins (250 mg) were used as starting material. Initial experiments demonstrated quantities of cytosolic proteins greater than 150 mg resulted in excessive precipitation during preparative IEF using the Rotofor apparatus. Moreover, increasing the detergent concentration of the IEF buffer did not solve this problem. Therefore, two preparative IEF runs were performed using 100 mg and 150 mg of the cytosolic proteins. A smaller total quantity of cytosolic protein was used in order to minimize the number of fractions that required pooling and to reduce potential distortion of IEF resolution. The 20 fractions collected from each run were analyzed by SDS-PAGE and silver staining, and like fractions were pooled. A similar problem of protein precipitation was not encountered with the highly soluble CFPs, and 500 mg of CFP was fractionated in a single preparative IEF run. The pH range of the fractions was 3.1 to 12.1 for CFPs and 3.9 to 12.3 for the cytosolic proteins. Analysis of both the culture filtrate and cytosolic protein fractions by SDS-PAGE demonstrated considerable overlap in those fractions at the extreme ends of the pH gradient (3.0 to 4.5 and 10.0 to 12.5). This was likely due to poor resolution by the Rotofor at the ends of the pH range, coupled with the large protein loads used. These overlapping fractions were pooled, resulting in 16 and 13 fractions of CFPs and cytosolic proteins, respectively. Efficient separation was achieved over a broad pH range. The protein content of the IEF fractions varied from 2.9 mg to 34.5 mg (CFPs), and 0.2 mg to 6.3 mg (cytosolic proteins), with the highest protein concentrations observed for fractions in the pH range of 3.8 to 5.1 for CFPs and 5.5 to 6.2 for cytosolic proteins. This is consistent with migration of the proteins of these subcellular fractions by 2-D PAGE.

Separation of IEF fractions in the second dimension was achieved by preparative SDS-PAGE. This resolved proteins into narrow molecular mass fractions. Each IEF fraction was applied to preparative 15% SDS-polyacrylamide gels, and after electrophoresis the proteins were recovered by electroelution using the Whole Gel Elutor. For each IEF fraction 30 preparative SDS-PAGE fractions were collected. However, within individual preparative SDS-PAGE runs, those proteins migrating at 14 kDa or less showed significant overlap. This overlap was also observed when the lower molecular weight fractions were resolved on 10-20% tricine gels. Thus, overlapping fractions in this molecular mass range were pooled. The 2-D LPE of the culture filtrate and cytosolic proteins resulted in 335 and 299 fractions, respectively, with each fraction containing 10 to 545 μg of protein.

EXAMPLE III

Production of IFNγ in Response to 2-D LPE Fractions

Prior to testing for T cell stimulation the 2-D LPE fractions were filter sterilized, aliquoted and lyophilized. Previously, it had been demonstrated that proteins isolated with the Whole Gel Eluter were relatively free of SDS and were suitable for direct use in T cell assays (Andersen et al., supra). Analysis of lymphocytes from uninfected C57B1/6 mice by microscopy and assessment of cell growth using the Alamar Blue redox reaction (Ahmed, S A et al., *J. Immunol. Methods*. 1994, 170:211-224) revealed that the SDS concentrations present in these 2-D LPE fractions did not adversely affect the cells, consistent with the findings of others.

Figure 2:
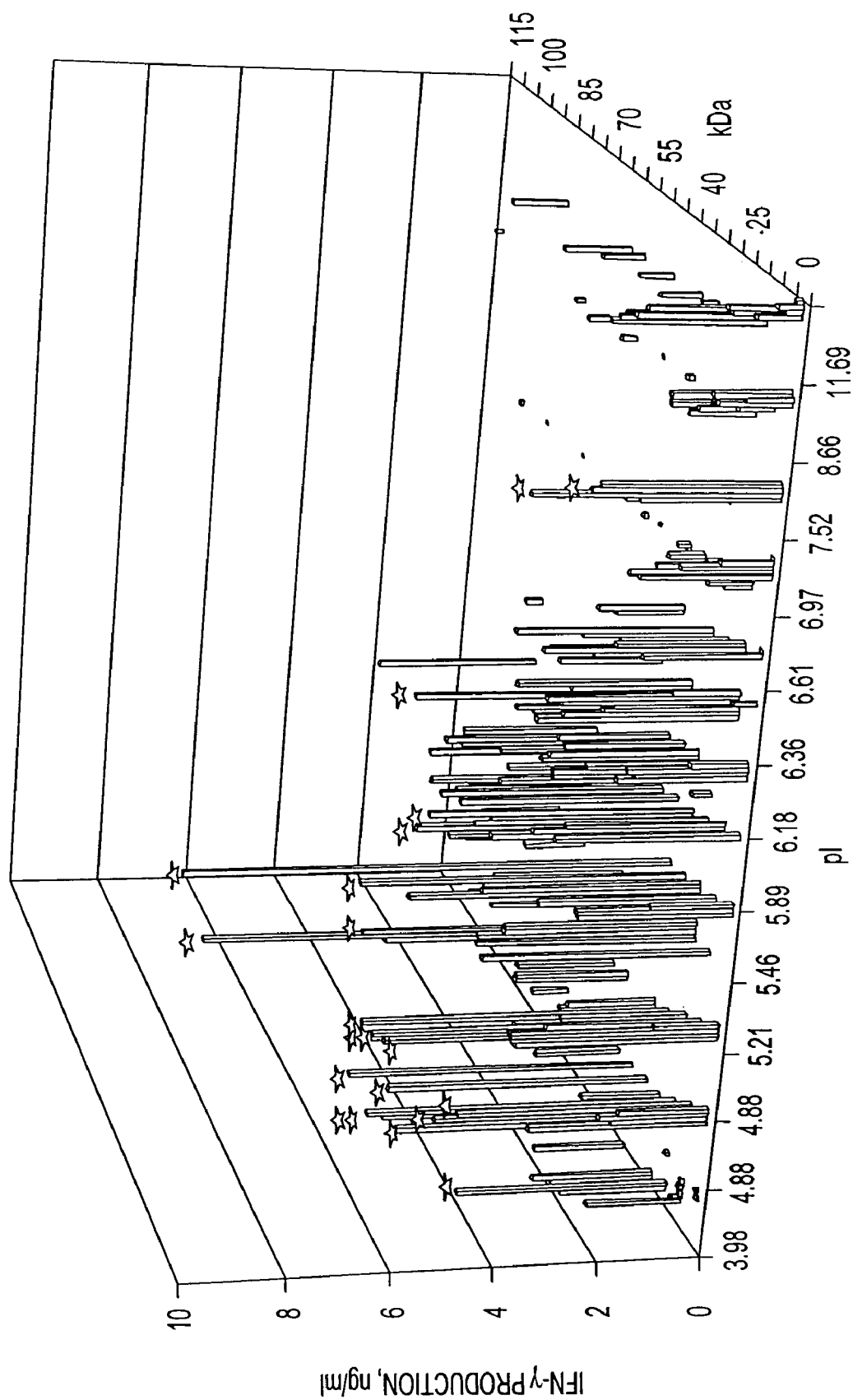

To assess T-cell reactivity to the 2-D LPE fractions, proteins were aliquoted (2 μg/well) in triplicate in 96 well plates and incubated for four days with the lymphocytes Mtb infected or uninfected mice, at which time the level of IFNγ present in the culture supernatant was measured. IFNγ production is a primary readout for T-cell activation (Orme et al., 1993, supra). The specific reactivity of T cells to individual Mtb antigens changes over the course of infection (Cooper et al., supra)). Thus, the reactivity of cells harvested at days 10 and 40 post infection was evaluated. The measurement of IFNγ production in T cells from the day 10 post-infected animals revealed that a large number of culture filtrate and cytosol 2-D LPE fractions induced significant levels of IFNγ production (FIGS. 1 and 2). The level of this reactivity was between 0 and 28.7 ng/mL, and 0 and 9.6 ng/mL for the culture filtrate and cytosol fractions, respectively. It should be noted that unfractionated CFPs and cytosolic proteins induced 5.9 and 1.6 ng/mL of IFNγ, respectively, from the same cells. Moreover none of the 2-D LPE fractions induced significant IFNγ production (<207 pg/mL) from the lymphocytes of uninfected mice, demonstrating that the IFNγ responses of T cells from infected mice were antigen specific. We would have expected the whole unfractionated CFP and cytosolic proteins to stimulate an equal or higher IFNγ response than that induced by individual fractions. Given that the strongest IFNγ responses were induced by the lower molecular weight fractions, it is possible the molar concentration of stimulatory antigens in these fractions was greater than in the entire protein pool. It is also possible that an inhibitor (such as LAM) could have lowered the values obtained with these pools. In general, the 2-D LPE fractions of the CFPs stimulated stronger IFN responses than did the cytosolic proteins. For both the culture filtrate and cytosolic protein fractions the strongest IFNγ response was observed with fractions of <30 kDa and with those in the more acidic pI range. This pattern of reactivity was similar to that obtained by Gulle et al. (supra) for proteins of *M. bovis* BCG separated by 2-D PAGE and subsequently evaluated in a T cell proliferation assay. This observation agreed with previous reports that the most dominant T cell antigens of *M. tuberculosis* are associated with the lower molecular weight (<30 kDa) CFPs (Boesen et al., supra; Roberts et al., supra).

Figure 3:
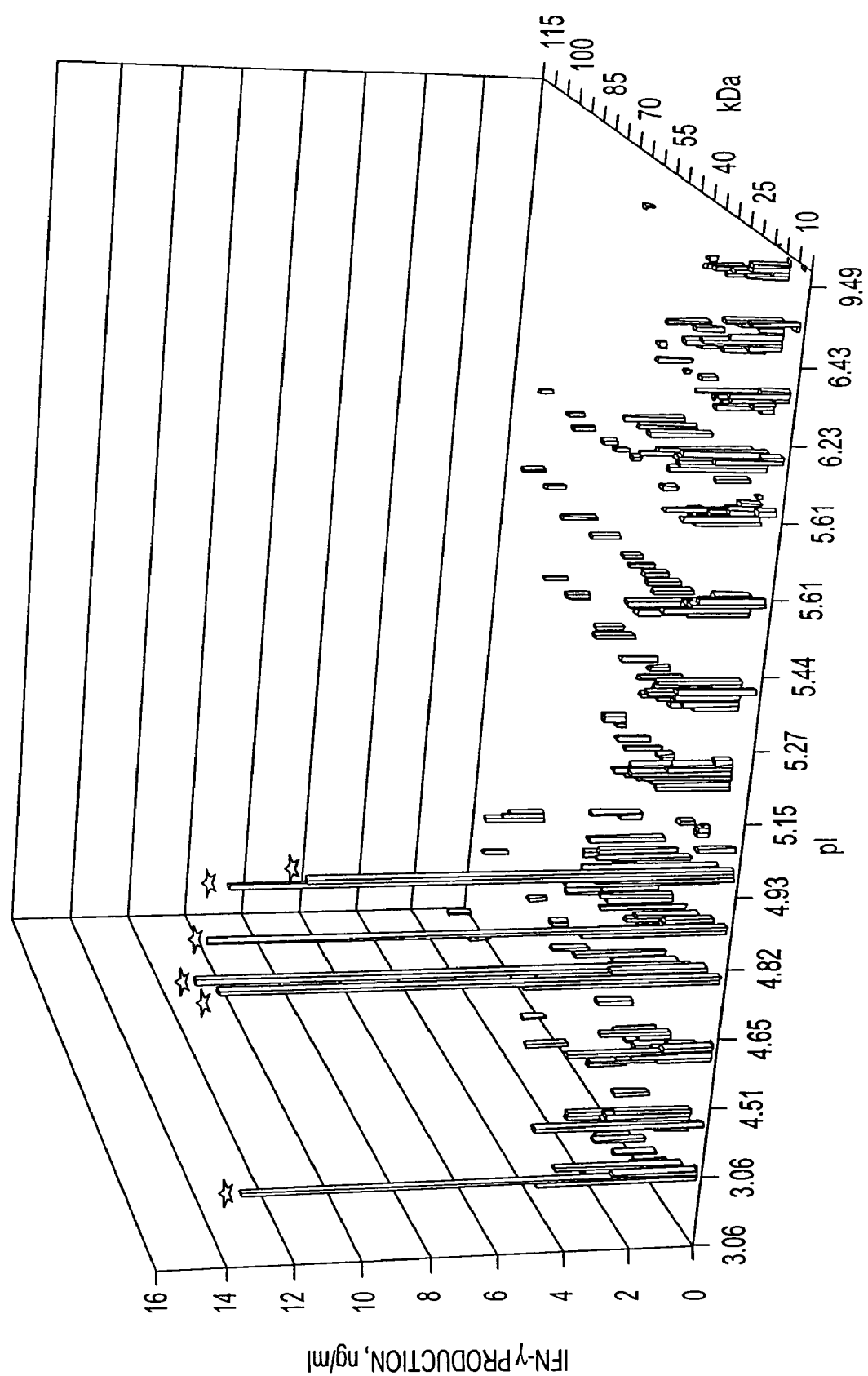
Figure 4:
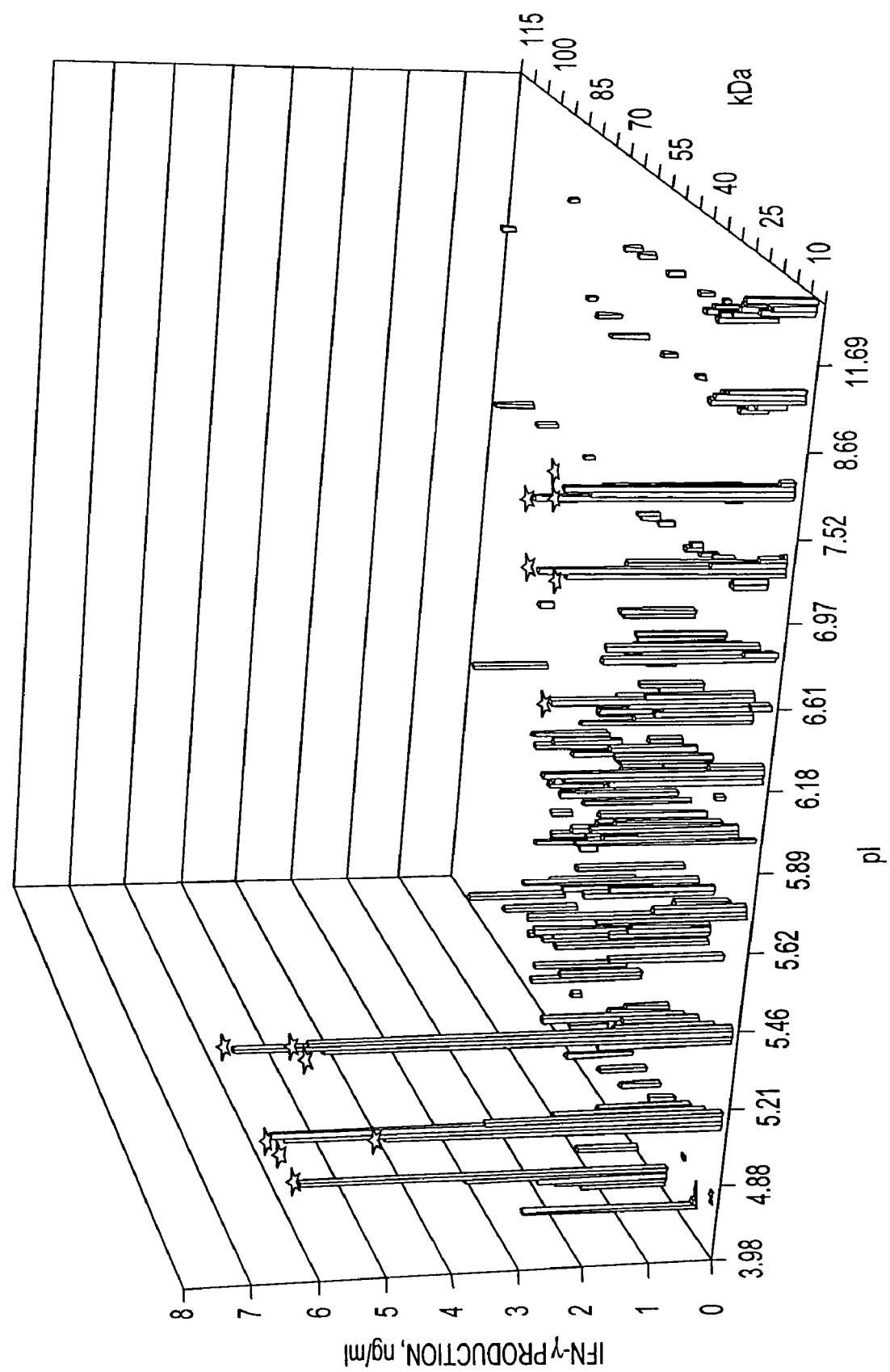

A number of the 2-D LPE fractions tested with spleen cells taken 40 day post-infection also induced significant IFNγ production (FIGS. 3 and 4). However, the pattern of reactivity was much less complex than that observed using lymphocytes taken day 10 post-infection. Those 2-D LPE fractions that stimulated the strongest T cell response later in the infection were also strong inducers of IFNγ in the day 10 group, and none of the antigen fractions were specific to the day 40 post-infected animals. These data confirm that the T cell reactivity to specific *M. tuberculosis* antigens changes over the course of the infection and that a select subgroup of proteins has the capacity to sustain a T cell response (Cooper et al., supra). It is likely that responsiveness to a larger number of antigen fractions at day 10 reflects the relative abundance of these antigens within the spleen (or other sites in the immune system) while the bacteria are actively dividing. Once bacterial growth is contained, the supply of antigens becomes limited, thus reducing T cell responses at later time points

EXAMPLE IV

Molecular Characterization of Dominant T Cell Immunogens

In total, 37 2-D LPE fractions were found to induce IFNγ responses that were at least three-fold greater than average response to all culture filtrate fractions or cytosol fractions. These more stimulatory fractions were selected for molecular characterization of their proteins. Analysis by 2-D PAGE and silver nitrate staining demonstrated the presence of one to seven proteins in each fraction. Moreover, the occurrence of multiple proteins in a fraction was primarily a consequence of incomplete resolution by preparative IEF.

Multiple strategies were employed for the identification of the *M. tuberculosis* protein antigens. For fractions containing more than one protein spot, 2-D PAGE was performed and the gels stained with Coomassie Brilliant Blue. Individual protein spots were excised, followed by in gel digestion with trypsin (Hellman et al., supra), and analysis of peptide fragments by LC-MS or LC-MS-MS. In some instances it was not possible to achieve complete separation of multiple protein spots. Thus for these fractions a gel slice containing more than one spot was digested and the identification of the protein mixture was achieved by analysis of the MS-MS data using the SEQUEST software (Ducret et al., *Protein Sci.* 1998, 1:106-719; McCormack, A L et al., *Anal. Chem.* 1997, 69:767-77631). Alternatively, for those fractions containing a single protein species an aliquot (~5 μg) was directly digested with trypsin and analyzed. The data from protein digests analyzed by LC-MS was searched against the *M. tuberculosis* proteome database using the MS Fit program (Baker et al., supra), and protein identification was accomplished by matching the experimental molecular mass (m/z) of 3 to 15 peptides to the mass of predicted tryptic fragments of *M. tuberculosis* proteins. The proteins are listed in Tables 1 and 2, above. Previous studies demonstrated that proteins are accurately identified using as few as 3-4 experimentally determined peptide masses (Pappin, D J et al., *Curr. Biol.* 1993, 3:327-332). The validity of protein identification was dictated by the MOWSE score assigned by the MS Fit program. All proteins identified by MS Fit in this study had a MOWSE score greater than $1\times10^3$.

When LC-MS-MS data was collected for digests of individual proteins or protein mixtures the data was searched against the *M. tuberculosis* proteome database using the SEQUEST software. Identification of proteins by this method was often achieved with MS-MS data from only a few (1 to 6) peptides. The Xcorr and ΔCn values assigned by SEQUEST determined the reliability of the MS-MS data for each peptide and the accompanying protein identification. The Xcorr is the raw correlation score, and is directly related to the number of fragment ions match (Ducret, A. et al., supra), whereas the ΔCn is the difference in the correlation score of the top two candidate proteins. When the difference ΔCn between the first and second ranked peptides is greater than 0.1, the first sequence is considered to be accurate with high probability (Eng et al., supra). All peptides assigned to a specific *M. tuberculosis* gene product based on the experimentally derived MS-MS fragmentation pattern yielded ΔCn values greater than 0.1, and their Xcorr scores were generally greater than 2. In a small number of instances the MS-MS data of only one peptide was used to determine protein identity of the proteins shown in Tables 1 and 2. (See Tables 1 and 2 of Covert et al., supra for additional detail). In such cases, additional information such as observed molecular weight and pI of the protein, was used with the Xcorr and ΔCn values to conclude the identity of the protein.

In all 16 and 18 proteins were identified in the immunodominant 2-D LPE fractions of the culture filtrate and cytosol, respectively (Tables 1 and 2). Several of the proteins identified (ModD, PhoS1, GroES, GroEL2, MPT 64, ESAT6, and FbpA, B and C2) have been shown by others to serve as T cell antigens (Thole, J et al., In: Ratledge, C et al., (eds), *Mycobacteria Molecular Biology and Virulence*. Blackwell Science, Oxford, UK 1999, pp. 356-370), though not in vivo boosting molecules for use in BCG-vaccinated subjects.

Two proteins (Rv1932 and Rv1827) elucidated herein were recently revealed to be T cell antigens by a similar strategy (Weldingh et al., supra). Many of the identified proteins were found in more than one immunodominant 2-D LPE fraction. This was particularly true for the cytosol fractions where IEF separation was more complex. Multiple fractions containing the same antigen were generally adjacent to each other. The exception to this was where GroEL2 was found in a high molecular weight fraction (D-30) and low molecular weight fractions (D-12, E-11 and E-13) (Table 2 of Covert et al.). The lower molecular weight fractions were hypothesized to possess break down products of GroEL2. Additionally, some proteins identified in the culture filtrate fractions were also found in immunodominant cytosol fractions. While a more thorough separation of proteins may have been desirable, the repeated identification of a small number of well-known and unknown antigens enhanced the level of confidence in this methodology. Equally exciting was the fact that this approach identified a large number of proteins not previously known to be T cell antigens, particularly in the cytosol. While the majority of the novel T cell antigens were assigned to open reading frames of unknown function, some, such as AhpC2, RplL, FixA, and FixB have functions predicted by sequence homology (Cole et al., supra). The FixA and FixB proteins are proposed to participate in β-oxidation of fatty acids, and AhpC2 a putative alkylhydroperoxidase may possess antioxidant activity that contributes to intracellular survival of the bacillus. Of note is RplL (Rv0652), a putative 50S ribosomal protein. The *Brucella melitensis* homologue of this protein has been shown to be a major antigen that induces delayed type hypersensitivity and is useful in diagnosing brucellosis (Bachrach, G et al., *Infect. Immun.* 1994, 62:5361-5366). However, the T cell reactivity of the *B. melitensis* RplL homologue is dependent on post-translational modification of the protein. While it is not known whether *M. tuberculosis* RplL possesses a similar modification, other proteins of *M. tuberculosis* are known to be glycosylated (Dobos et al., supra) and this type of modification has been demonstrated to effect T cell reactivity (Horn, C et al., *J. Biol. Chem.* 1999, 274: 32023-23030). Unlike high throughput recombinant methodologies, a proteomics approach with native molecules will detect antigen reactivity that is dependent on the post-translational modification of the protein. Of the 30 individual proteins identified in this study, 17 of them (Rv0057, Rv3841, Rv1352, Rv1810, Rv3044, Rv0054, Rv0652, Rv3029c, Rv3028Rv2428, Rv2626c, Rv1211, Rv1240, Rv1626, Rv0733, Rv2461c, and Rv0952) represent a pool of new T cell immunogens of *M. tuberculosis* that induce increased resistance to infection in a subject previously immunized with BCG (as exemplified with Ag85A (=Rv3804c) below). Mycobacterial lipids or lipoglycans may have also contributed to the IFNγ response for some of these novel proteins. However, most of these lipid molecules migrate over a broad acidic pH range (pH 4 to 6), and not all fractions in this range gave high IFNγ responses. Additionally, lymphocytes from uninfected animals did not respond to any of the protein fractions whereas most lipid molecules stimulate innate and non-specific immune responses. This suggests that the IFNγ responses were manifestations of an acquired immune response to a protein or proteins within the 2-D LPE fractions and were not responses to non-protein contaminants. Use of recombinant, cloned proteins (as disclosed herein) and further immunological characterization will increase our understanding of these proteins as vaccine compositions (or skin test antigens for diagnosis).

EXAMPLE V

Ag85A (Rv3804c Product) Induces Resistance to Infection by Virulent *M. tuberculosis*

Figure 5:
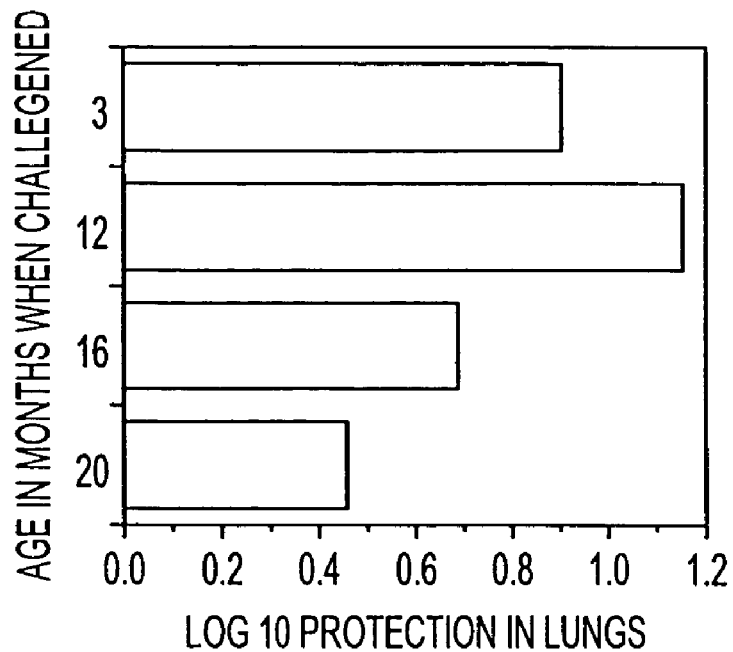
FIG. 5 is a graph showing that the protective effect of BCG gradually wanes as animals grow older. C57B1/6 mice were vaccinated subcutaneously with $10^6$ *M. bovis* BCG strain Pasteur at 6 weeks of age and challenged at the indicated time points by exposure to an aerosol delivered infection of approximately 50 bacteria of *M. tuberculosis* H37Rv. Mice were euthanized thirty days later and bacterial counts in the lungs determined by plating on Middlebrook 7H11 agar. Levels of protection to the challenge were determined by calculating mean values ($\log_{10}$) of 4-5 mice and subtraction from values obtained in unvaccinated, age-matched controls.

The protection conferred against an aerosol challenge infection by virulent *M. tuberculosis* in mice of increasing age is shown in FIG. 5. Mice had been vaccinated with BCG at 6-8 weeks of age and were challenged at various ages thereafter.

In mice 3 and 12 months of age a 10-fold reduction in bacterial load in the lungs was consistently observed thirty days after challenge.

Figure 6:
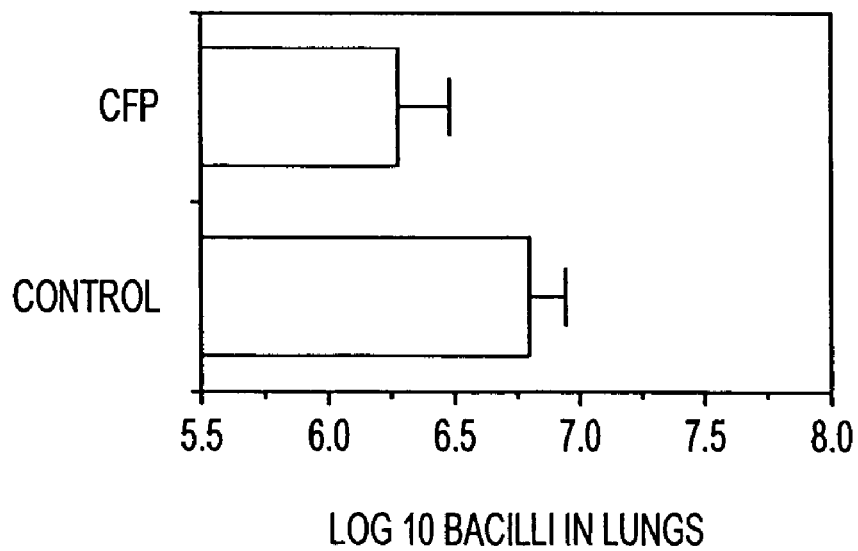
FIG. 6 is a graph showing that vaccination of 20 month old mice with a culture filtrate protein (CFP) vaccine resulted in only a marginal reduction in the lung bacterial load after aerosol challenge (as in FIG. 5). Mice were vaccinated twice, three weeks apart, and then rested four weeks before aerosol infection. The vaccine consisted of 100 μg purified mid-log phase CFPs from *M. tuberculosis* H37Rv emulsified in monophosphoryl lipid A adjuvant solubilized in 0.02% triethanolamine plus 100 μg rIL-2 cytokine. Bacterial counts were determined as above thirty days after challenge.

C57B1/6 mice typically live for an average of 22-24 months. In their second year of life this resistance gradually wanes, dropping to 0.7 logs at 16 months, and to 0.35 logs at 20 months of age. As shown in FIG. 6, resistance in the lungs of previously unvaccinated elderly mice was increased by treatment with mycobacterial culture filtrate protein (CFP)-based subunit vaccine (A. D. Roberts, et al., *Immunology* 85:502-8 (1995)), but the improvement was only marginal.

Figure 7:
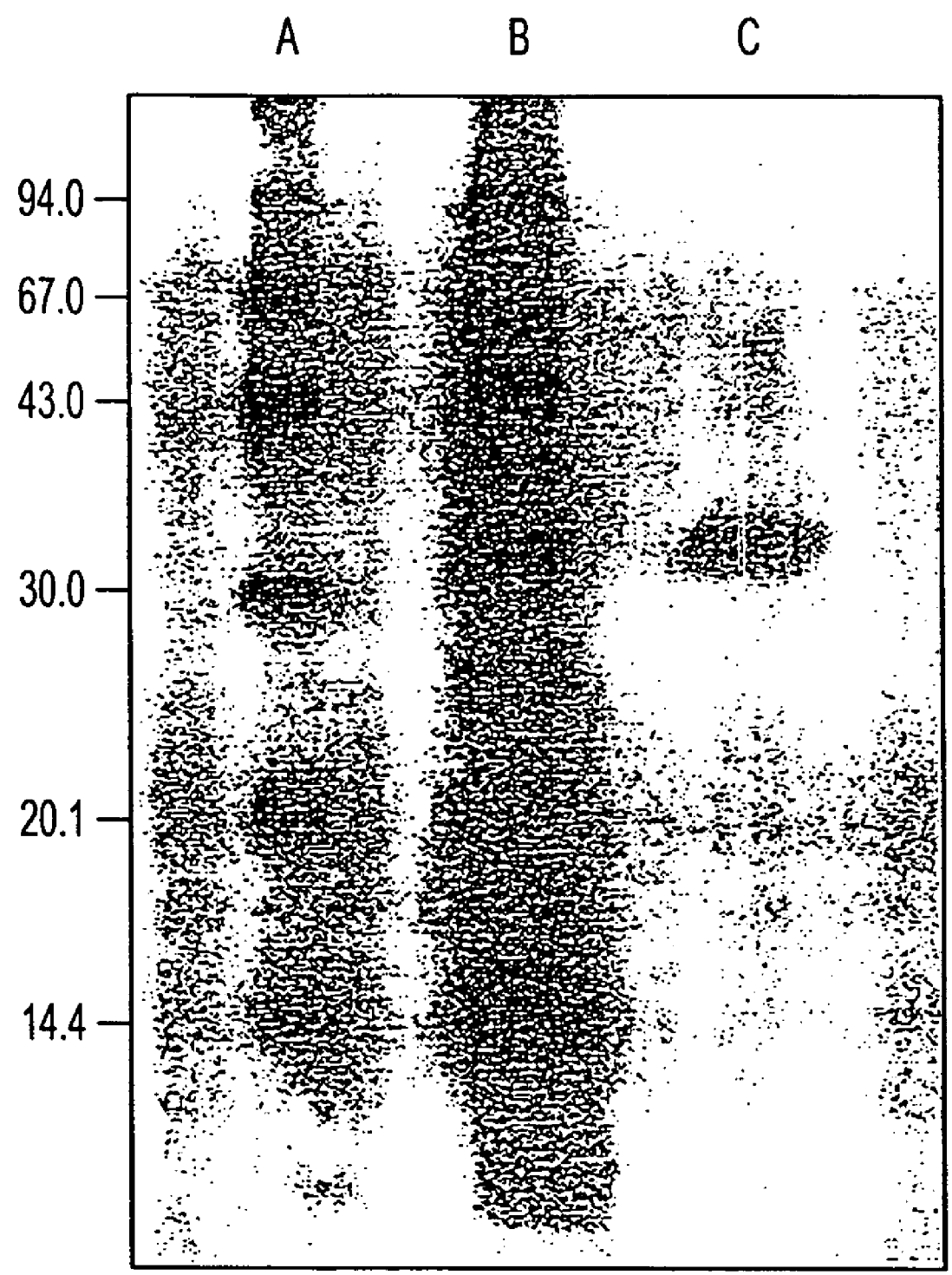
FIG. 7 shows an SDS-PAGE gel of enriched Mtb culture filtrate proteins (lane B) and purified Ag85A (lane C). Lane A has molecular weight markers.

Because the fact that the majority of T cells that are involved in protection in the lungs of young mice recognize the Ag85 proteins (Cooper et al., supra), the present inventors conceived that this antigen would restimulate existing immunological memory in BCG-vaccinated subjects. To achieve this, native Ag85A was purified as previously described (Belisle et al., supra) and shown to be pure by gel electrophoresis (FIG. 7).

Figure 8:
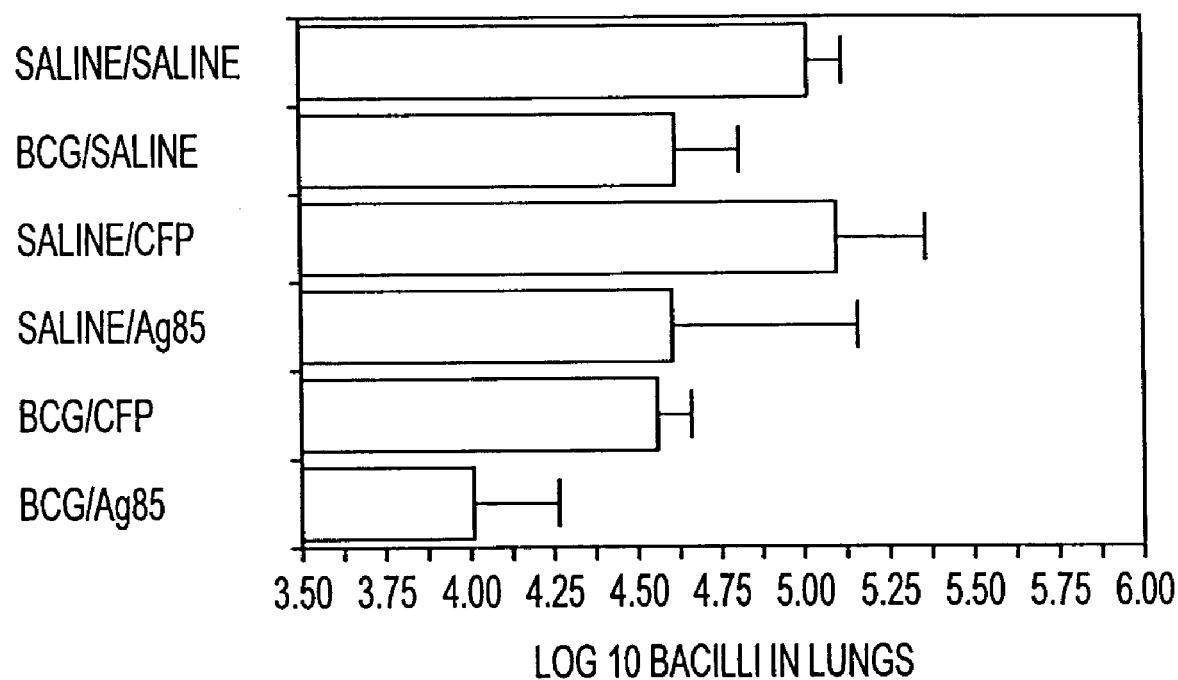
FIG. 8 is a graph showing that vaccination followed by boosting with Ag85A improves resistance to aerosol challenge compared to BCG vaccination alone. Mice were inoculated with BCG as above at 8 weeks of age; controls were injected with saline. At 9 and 15 months of age, they were boosted with either CFP or Ag85A in an adjuvant vehicle (monophosphoryl Lipid A/rIL-2). Mice were challenged by aerosol at 20 months of age. Only the Ag85A-treated group showed a statistically significant diminution of lung bacterial counts relative to the saline controls ($p<0.001$).
Figure 9B:
FIG. 9 presents a set of representative photomicrographs of lung tissue from vaccine boosted mice following aerosol infection with *M. tuberculosis*. All plates were stained with hematoxylin and eosin, and all size bars represent 10 μm.
Figure 9D:
Figure 9A:
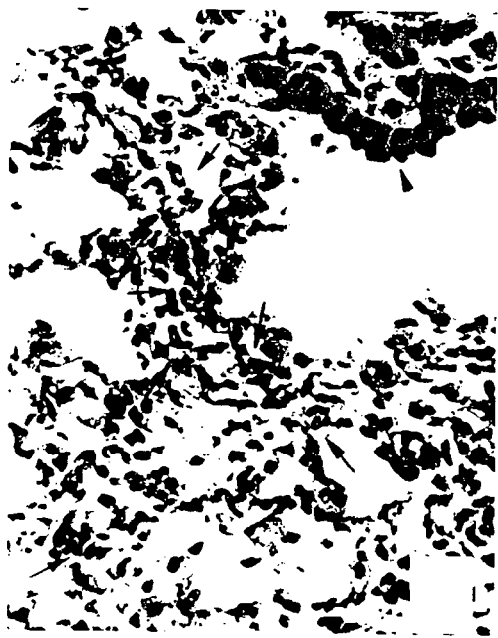
Figure 9C:

As shown in FIG. 8, mice vaccinated at 3 months of age and then challenged by an aerosol containing *M. tuberculosis* organisms at 20 months of age were marginally protected (0.47 log) as was anticipated. Boosting with the CFP vaccine (a protein mixture of which approximately 10% consists of the Ag85 complex) had no effect on the subsequent bacterial resistance. However, boosting with purified Ag85A resulted in a 10-fold (1 log) reduction in lung bacterial counts (p<0.001).

Histologic examination of the infected lungs of these animals revealed a further unexpected benefit of the boosting vaccination. In both BCG control and BCG/Ag85 boosted mice the gradual development of a lymphocytic granulomatous response proceeded as expected (FIG. 9). However, careful examination of lesions revealed numerous small foci or pockets of neutrophils distributed throughout the lesions in the BCG control animals.

In contrast, lungs of the Ag85A-boosted mice were mostly devoid of these lesions with only an occasional (usually solitary) neutrophil detected.

These results suggested that not only can mid-life boosting vaccination restore specific antimicrobial resistance in elderly mice to levels expressed by young BCG-vaccinated animals, but lung tissue damage and degeneration, which is almost certainly the basis of the influx of neutrophils into the lesions of the old mice, was also dramatically reduced.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method for boosting the immune response to *Mycobacterium tuberculosis* (Mtb) in a mammal which has been vaccinated neonatally or early in life with BCG, to increase the resistance of said mammal to Mtb infection, said method comprising:

administering to a mammal in need of said boosting, an immunogenically effective amount of an Mtb immunogenic protein composition that comprises one or more purified Mtb proteins or homologues of said proteins, which protein or homologue is characterized in that it:

(a) stimulates significant interferon-γ secretion by T lymphocytes of a mammal which has been immunized with Mtb antigens; and/or (b) when administered to a mammalian subject at an age when immunity induced by said BCG vaccination is waning, significantly increases the resistance of said subject to Mtb infection, thereby increasing the resistance of said mammal to Mtb infection.

2. The method of claim 1 wherein said mammal is a human.

3. The method of claim 2 wherein the administering is performed between about 1 year and about 10 years after the BCG vaccination.

4. The method of claim 2 wherein the administering is performed when said human is at least about 10 years of age.

5. The method of claim 4 wherein the administering is performed when said human is at least about 15 years of age.

6. The method of claim 5 wherein said administering is performed when said human is at least about 20 years of age.

7. The method of claim 1 wherein the immunogenic protein composition comprises one or more of said purified Mtb proteins selected from the group consisting of the product of the Mtb gene Rv3804c, Rv1886c, Rv0129c, Rv1860, Rv0934, Rv0577, Rv1827, Rv3841, Rv1932, Rv1352, Rv3418c, Rv3875, Rv1810, Rv1980c, Rv0350, Rv3044, Rv0054, Rv0652, Rv3029c, Rv3028c, Rv2428, Rv0440Rv2031c, Rv2626c, Rv1211, Rv1240, Rv1626, Rv0733, Rv2461c, and Rv0952.

8. The method of claim 1 wherein the immunogenic protein composition comprises one or more of said purified Mtb proteins selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30 and SEQ ID NO:31, wherein, when said protein is an Mtb secreted protein, the sequence is the truncated sequence of the above sequences from which the signal sequence has been removed.

9. The method of claim 8, wherein the proteins are selected from the group consisting of SEQ ID NO:6; SEQ ID NO:8; SEQ ID NO:10; SEQ ID NO:13; SEQ ID NO:16; SEQ ID NO:17; SEQ ID NO:18; SEQ ID NO:19; SEQ ID NO:20; SEQ ID NO:21; SEQ ID NO:24; SEQ ID NO:25; SEQ ID NO:26; SEQ ID NO:27; SEQ ID NO:28;SEQ ID NO:29 and SEQ ID NO:30.

10. The method of claim 9, wherein the proteins are selected from the group consisting of SEQ ID NO:6; SEQ ID NO:7; SEQ ID NO:10; SEQ ID NO:13; SEQ ID NO:24; SEQ ID NO:25 and SEQ ID NO:27.

11. The method of claim 7 wherein the immunogenic protein composition further includes Ag85A (SEQ ID NO:31).

12. The method of claim 7 wherein the immunogenic protein composition is a single Mtb protein.

13. The method of claim 12 wherein the single protein is Ag85A (SEQ ID NO:31).

14. The method of claim 1 wherein the immunogenic composition further comprises an adjuvant or an immunostimulatory protein different from said immunogenic Mtb protein.

15. The method of claim 14 wherein said immunostimulatory protein is a cytokine.

16. The method of claim 15 wherein said cytokine is interleukin 2 or GM-CSF.

17. The method of claim 14, wherein said adjuvant is selected from the group consisting of
 (a) ISAF-1 (5% squalene, 2.5% pluronic L121, 0.2% Tween 80) in phosphate-buffered solution with 0.4 mg of threonyl-muramyl dipeptide;
 (b) de-oiled lecithin dissolved in an oil;
 (c) aluminum hydroxide gel;
 (d) a mixture of (b) and (c)
 (e) QS-21; and
 (f) monophosphoryl lipid A adjuvant.

18. The method of claim 17 wherein the adjuvant is monophosphoryl lipid A adjuvant solubilized in 0.02% triethanolamine.

19. The method of claim 17 wherein said composition further comprises recombinant interleukin-2.

20. An immunogenic composition useful for boosting the immune response to Mtb in a mammal which has been vaccinated neonatally or early in life with BCG, to increase the resistance of said mammal to Mtb infection compared to the resistance of a mammal to BCG vaccination, said composition comprising one or more purified Mtb proteins selected from the group consisting of:
 (a) the product of the Mtb gene Rv1352,
 (b) the product of the Mtb gene Rv1810,
 (c) the product of the Mtb gene Rv3044,
 (d) the product of the Mtb gene Rv0054,
 (e) the product of the Mtb gene Rv3028c,
 (f) the product of the Mtb gene Rv2626c,
 (g) the product of the Mtb gene Rv1240,
 (h) the product of the Mtb gene Rv1626,
 (i) the product of the Mtb gene Rv0733,
 (j) the product of the Mtb gene Rv2461c,
 (k) the product of the Mtb gene Rv0952,
 (l) the product of the Mtb gene Rv3418c,
 (m) the product of the Mtb gene Rv0350, and
 (n) a homologue of any one of proteins (a)-(k).

21. An immunogenic composition comprising two or more of the following purified Mtb proteins or homologues:
 (i) the purified Mtb proteins or homologues of the composition of claim 20,
 (ii) a purified Mtb protein product of the Mtb gene Rv1860, Rv0934, Rv3875, Rv2428, Rv0440, Rv2031c or Rv1211.

22. An immunogenic composition comprising three or more of said purified Mtb proteins or said homologues of the composition of claim 21.

23. The composition of claim 20 wherein the one or more purified proteins
 (a) comprises a sequence selected from the group consisting of SEQ ID NO: 10, SEQ ID NO:13, SEQ ID NO:16, SEQ ID NO:17, SEQ ID NO:20, SEQ ID NO:24, SEQ ID NO:26, SEQ ID NO:27, SEQ ID NO:28, SEQ ID NO:29, and SEQ ID NO:30; or
 (b) consists of a sequence SEQ ID NO:11 or SEQ ID NO:15, and
wherein, when said protein is an Mtb secreted protein, the sequence is a truncated sequence of the above sequences from which the signal sequence has been removed.

24. The composition of claim 23 wherein the one or more proteins has a sequence selected from the group consisting of SEQ ID NO:10; SEQ ID NO:13; SEQ ID NO:24; SEQ ID NO:25 and SEQ ID NO:27.

25. The composition of claim 20 which further includes Ag85A (SEQ ID NO:31).

26. An immunogenic composition that comprises
 (a) a purified Mtb protein or homologue according to claim 20,
 (b) a product of the Mtb gene Rv0934, Rv2428, Rv0440, Rv2031c, orRv1211, or of a homologue of said Mtb gene Rv0934, Rv2428, Rv0440, Rv2031c, or Rv1211, and
further comprises an immunostimulatory protein different from said Mtb proteins.

27. The composition of claim 26 wherein said immunostimulatory protein is a cytokine.

28. The composition of claim 27 wherein said cytokine is interleukin 2 or GM-CSF.

29. The composition of claim 27 wherein said adjuvant is selected from the group consisting of:
 (a) ISAF-1 (5% squalene, 2.5% pluronic L121, 0.2% Tween 80) in phosphate-buffered solution with 0.4 mg of threonyl-muramyl dipeptide;
 (b) de-oiled lecithin dissolved in an oil;
 (c) aluminum hydroxide gel;
 (d) a mixture of (b) and (c)
 (e) QS-21; and
 (f) monophosphoryl lipid A adjuvant.

30. The composition of claim 29 wherein the adjuvant is monophosphoryl lipid A adjuvant solubilized in 0.02% triethanolamine.

31. The composition of claim 29 that further comprises recombinant interleukin-2.

32. The composition of claim 21, wherein the two or more purified Mtb proteins are selected from the group consisting of the product of the following Mtb genes: Rv1352, Rv3418c, Rv1810, Rv0350, Rv3044, Rv0054, Rv3028c, Rv2626c, Rv1240, Rv1626, Rv0733, Rv2461c, and Rv0952.

33. The composition of claim 22, wherein the three or more purified Mtb proteins are selected from the group consisting of the product of the Mtb gene: Rv1352, Rv3418c, Rv3875, Rv1810, Rv0350, Rv3044, Rv0054, Rv3028c, Rv2626c, Rv1240, Rv1626, Rv0733, Rv2461c, and Rv0952.

34. The composition of claim 21 wherein the two or more purified proteins have a sequence selected from the group consisting of SEQ ID NO:3, SEQ ID NO:4, SEQ ID NO:5, SEQ ID NO:7, SEQ ID NO:10, SEQ ID NO:11, SEQ ID NO:12, SEQ ID NO:13, SEQ ID NO:15, SEQ ID NO:16, SEQ ID NO:17, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30, wherein, when said protein is an Mtb secreted protein, the sequence is a truncated sequence of the above sequences from which the signal sequence has been removed.

35. The composition of claim 22 wherein the three or more purified proteins have a sequence selected from the group consisting of SEQ ID NO:3, SEQ ID NO:4, SEQ ID NO:5, SEQ ID NO:7, SEQ ID NO:10, SEQ ID NO:11, SEQ ID NO:12, SEQ ID NO:13, SEQ ID NO:15, SEQ ID NO:16, SEQ ID NO:17, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30, wherein, when said protein is an Mtb secreted protein, the sequence is a truncated sequence of the above sequences from which the signal sequence has been removed.

36. The composition of claim 23 that further comprises (i) an adjuvant or (ii) an immunostimulatory protein that is not an Mtb protein.

37. An immunogenic composition that comprises a purified Mtb protein or homologue of the composition of claim 20, a product of the Mtb gene Rv1860, Rv0934, Rv0440, Rv2031c, or Rv1211, or a product of a homologue of said Mtb genes and further comprises an adjuvant.

38. The composition of claim 34 which further comprises SEQ ID NO:31.

39. The composition of claim 35 which further comprises SEQ ID NO:31.

* * * * *

UNITED STATES PATENT AND TRADEMARK OFFICE
CERTIFICATE OF CORRECTION

PATENT NO. : 7,288,261 B2  Page 1 of 1
APPLICATION NO. : 10/332512
DATED : October 30, 2007
INVENTOR(S) : Ian M. Orme and John T. Belisle It is certified that error appears in the above-identified patent and that said Letters Patent is hereby corrected as shown below:

Column 3, line 31, before "it" insert the following text --, other than BCG, and --.

Column 3, line 31-33, cancel the text: "This paper has been widely criticized for its lack of proper scientific methodology."

Signed and Sealed this

Seventh Day of July, 2009

JOHN DOLL
*Acting Director of the United States Patent and Trademark Office*